United States Patent
Hartung et al.

(10) Patent No.: US 8,993,630 B2
(45) Date of Patent: Mar. 31, 2015

(54) SUBSTITUTED SULPHONAMIDO PHENOXYBENZAMIDES

(75) Inventors: Ingo Hartung, Erkrath (DE); Marion Hitchcock, Berlin (DE); Florian Puhler, Berlin (DE); Gerhard Siemeister, Berlin (DE); Roland Neuhaus, Berlin (DE)

(73) Assignee: Bayer Intellectual Property GmbH, Monheim (DE)

( * ) Notice: Subject to any disclaimer, the term of this patent is extended or adjusted under 35 U.S.C. 154(b) by 373 days.

(21) Appl. No.: 13/128,274

(22) PCT Filed: Oct. 28, 2009

(86) PCT No.: PCT/EP2009/007726
§ 371 (c)(1),
(2), (4) Date: May 9, 2011

(87) PCT Pub. No.: WO2010/051933
PCT Pub. Date: May 14, 2010

(65) Prior Publication Data
US 2011/0218219 A1    Sep. 8, 2011

(30) Foreign Application Priority Data
Nov. 10, 2008 (EP) .................................... 08168724

(51) Int. Cl.
| | | |
|---|---|---|
| *A01N 41/06* | (2006.01) | |
| *A61K 31/18* | (2006.01) | |
| *A01N 43/40* | (2006.01) | |
| *C07C 303/00* | (2006.01) | |
| *C07C 307/00* | (2006.01) | |
| *C07C 309/00* | (2006.01) | |
| *C07C 311/00* | (2006.01) | |
| *C07D 213/72* | (2006.01) | |
| *C07C 311/08* | (2006.01) | |

(52) U.S. Cl.
CPC .................................... *C07C 311/08* (2013.01)
USPC ............. 514/602; 514/605; 514/349; 564/80; 564/99; 546/297

(58) Field of Classification Search
USPC ........ 514/602, 605, 349; 564/80, 99; 546/297
See application file for complete search history.

(56) References Cited

U.S. PATENT DOCUMENTS

| | | |
|---|---|---|
| 6,506,798 B1 | 1/2003 | Barrett et al. |
| 2009/0082328 A1 | 3/2009 | Li et al. |

FOREIGN PATENT DOCUMENTS

| | | |
|---|---|---|
| WO | WO 01/05392 A2 | 1/2001 |
| WO | WO 2007/014011 A2 | 2/2007 |
| WO | WO 2008/138639 A1 | 11/2008 |

OTHER PUBLICATIONS

J. G. Cannon Chapter Nineteen in Burger's Medicinal Chemistry and Drug Discovery, Fifth Edition, vol. I: Principles and Practice, Wiley-Interscience 1995, pp. 783-802, 784.*
Sheridan, R.P. "The Most Common Chemical Replacements in Drug-like Compounds" J. Chem.Inf.Comput. Sci., 2002, vol. 42, pp. 1034-1080.*
International Search Report of PCT/EP2009/007726 (May 4, 2010).

* cited by examiner

*Primary Examiner* — Kendra D Carter

(57) ABSTRACT

The present invention relates to substituted sulphonamido phenoxybenzamide compounds of general formula (I):

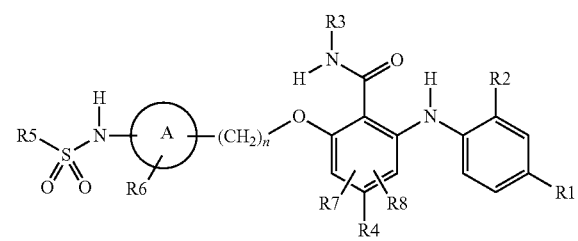

in which A, R1, R2, R3, R4, R5, R6, R7, R8 and n are as defined in the claims, to pharmaceutical compositions and combinations containing said compounds, to methods of preparing said compounds, and to the use of said compounds or compositions for treating hyper-proliferative and/or angiogenesis disorders, as a sole agent or in combination with other active ingredients.

11 Claims, No Drawings

SUBSTITUTED SULPHONAMIDO PHENOXYBENZAMIDES

FIELD OF THE INVENTION

The present invention relates to substituted sulphonamido phenoxybenzamide compounds of general formula (I) as described and defined herein, to methods of preparing said compounds, to pharmaceutical compositions and combinations comprising said compounds and to the use of said compounds for manufacturing a pharmaceutical composition for the treatment or prophylaxis of a disease, in particular of a hyper-proliferative and/or angiogenesis disorder, as a sole agent or in combination with other active ingredients.

BACKGROUND OF THE INVENTION

Cancer is a disease resulting from an abnormal growth of tissue. Certain cancers have the potential to invade into local tissues and also metastasize to distant organs. This disease can develop in a wide variety of different organs, tissues, and cell types. Therefore, the term "cancer" refers to a collection of over a thousand different diseases.

Over 4.4 million people worldwide were diagnosed with breast, colon, ovarian, lung, or prostate cancer in 2002 and over 2.5 million people died of these devastating diseases (Globocan 2002 Report). In the United States alone, over 1.25 million new cases and over 500,000 deaths from cancer were predicted in 2005. The majority of these new cases were expected to be cancers of the colon (~100,000), lung (~170,000), breast (~210,000) and prostate (~230,000). Both the incidence and prevalence of cancer is predicted to increase by approximately 15% over the next ten years, reflecting an average growth rate of 1.4% [1].

Accumulating evidence suggests that cancer can be envisioned as a "signaling disease", in which alterations in the cellular genome affecting the expression and/or function of oncogenes and tumor suppressor genes would ultimately affect the transmission of signals that normally regulate cell growth, differentiation, and programmed cell death (apoptosis). Unraveling the signaling pathways that are dysregulated in human cancers has resulted in the design of an increasing number of mechanism-based therapeutic agents [2]. Signal transduction inhibition as a therapeutic strategy for human malignancies has recently met with remarkable success, as exemplified by the development of Gleevec for the treatment of chronic myelogenous leukemia (CML) and gastrointestinal stromal tumors (GIST), heralding a new era of "molecularly-targeted" therapies [3-5].

The mitogen-activated protein kinase (MAPK) module is a key integration point along the signal transduction cascade that links diverse extracellular stimuli to proliferation, differentiation and survival. Scientific studies over the last twenty years have led to a quite detailed molecular dissection of this pathway, which has now grown to include five different MAPK subfamilies [extracellular signal-regulated kinases ERK-1/2, c-Jun-N-terminal kinases (JNKs), p38 kinases, ERK-3/4, and ERK-5], with distinct molecular and functional features [6-8]. While certain subfamilies, such as the p38 family, are becoming therapeutic targets in inflammatory and degenerative diseases, the MAPK cascade that proceeds from Ras to ERK-1/2 (the main mitogenic pathway initiated by peptide growth factors) is starting to emerge as a prime target for the molecular therapy of different types of human cancers [9-11], The MAPK pathway is aberrantly activated in many human tumors as a result of genetic and epigenetic changes, resulting in increased proliferation and resistance to apoptotic stimuli. In particular, mutated oncogenic forms of Ras are found in 50% of colon and >90% of pancreatic cancers [12]. Recently, BRAF mutations have been found in >60% of malignant melanoma [13]. These mutations result in a constitutively activated MAPK pathway.

The modular nature of the Raf/MEK/ERK cascade becomes less pleiotropic at the crossover point that is regulated by MEK [14]. No substrates for MEK have been identified other than ERK-1/2. Phosphorylated ERK is the product of MEK activity and thus its detection in cancer cells and in tumor tissues provides a direct measure of MEK inhibition. The selectivity of MEK for ERK1/2 coupled with the availability of antibodies specific for the dually phosphorylated and activated form of ERK, makes MEK an attractive target for anticancer drug development.

First-generation MEK inhibitors, PD98059 [15] and U0126 [16], do not appear to compete with ATP and thus are likely to have distinct binding sites on MEK; these compounds have been extensively used in model systems in vitro and in vivo to attribute biological activities to ERK1/2. A second-generation MEK1/2 inhibitor, PD184352 (now called CI-1040), has an $IC_{50}$ in the low nanomolar range, enhanced bioavailability, and also appears to work via an allosteric, non ATP-competitive mechanism [17]. Oral treatment with CI-1040 has been shown to inhibit colon cancer growth in vivo in mouse models [18] and this compound was evaluated in phase I/II clinical trials in humans where it eventually failed because of insufficient efficacy [19]. Allosteric MEK inhibitors have recently entered the clinic but were found to have limitations such as poor exposure profiles and/or toxicity issues. Small molecules MEK inhibitors have been disclosed, including in US Patent Publications Nos. 2003/0232869, 2004/0116710, 2003/0216420 and in U.S. patent application Ser. Nos. 10/654,580 and 10/929,295 each of which is hereby incorporated by reference. A number of additional patent applications have appeared in the last few years including U.S. Pat. No. 5,525,6625; WO 98/43960; WO 99/01421; WO 99/01426; WO 00/41505; WO 00/41994; WO 00/42002; WO 00/42003; WO 00/42022; WO 00/42029; WO 00/68201; WO 01/68619; WO 02/06213; WO 03/077914; WO 03/077855; WO 04/083167; WO 05/0281126; WO 05/051301; WO 05/121142; WO 06/114466; WO 98/37881; WO 00/35435; WO 00/35436; WO 00/40235; WO 00/40237; WO 01/05390; WO 01/05391; WO 01/05392; WO 01/05393; WO 03/062189; WO 03/062191; WO 04/056789; WO 05/000818; WO 05/007616; WO 05/009975; WO 05/051300; WO 05/051302; WO 05/028426; WO 06/056427; WO 03/035626; and WO 06/029862.

Despite advancements in the art, there remains a need for cancer treatments and anti-cancer compounds. More specifically, there remains a need for structurally novel MEK inhibitors with a balanced potency-properties profile. It would be especially desirable to identify novel MEK inhibitors which incorporate structural motifs which have not been previously exemplified as being compatible with potent MEK inhibition. It would be especially favorable if these structural motifs would further allow for improvement of MEK potency and/or modulation of compound properties (including physicochemical, pharmacodynamical and pharmacokinetical properties).

None of the prior art described or cited supra describe the substituted amido phenoxybenzamide compounds of general formula (I) of the present invention, as described and defined herein, and as hereinafter referred to as "compounds of the present invention", or their pharmacological activity. It has now surprisingly been found, and this constitutes the basis of the present invention, that said compounds of the present invention, which possess a substituted amido phenoxybenzamide moiety, have unexpected and advantageous properties, in particular, said compounds are potent and selective MEK inhibitors. Said compounds of the present invention inhibit activation of the MEK-ERK pathway and show anti-proliferative activity against cancer cells. Compounds and compositions described herein, including salts, metabolites, solvates, solvates of salts, hydrates, prodrugs such as esters, polymorphs, and stereoisomeric forms thereof, exhibit antiproliferative activity and are thus useful to prevent or treat the diseases or disorders associated with hyper-proliferation as described herein.

DESCRIPTION OF THE INVENTION

The present invention thus relates to compounds of general formula (I):

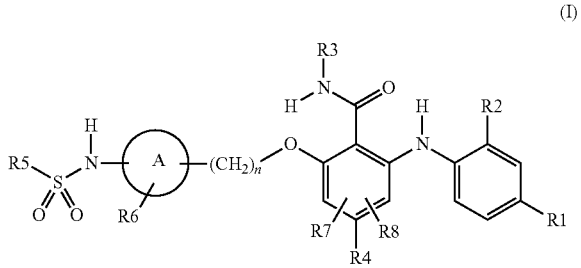

in which:
R1 is selected from the group comprising, preferably consisting of, halogen or —C≡C—H;
R2 is hydrogen, halogen or alkyl;
wherein at least one of R1 and R2 is halogen;
R3 is hydrogen or alkyl;
R4 is selected from the group comprising, preferably consisting of, halogen and cyano;
R5 is C2-C6 alkyl;
R6 is selected from the group comprising, preferably consisting of, hydrogen, halogen, cyano, alkoxy, amino, alkylamino, dialkylamino;
R7 and R8 independently from each other are hydrogen, halogen or alkyl;
A is selected from the group comprising, preferably consisting of, aryl and heteroaryl;
n is an integer from 0 to 2.

In accordance with a particular embodiment, the present invention relates to compounds of general formula (I), supra, in which:
R1 is halogen;
R2 is halogen;
R3 is hydrogen;
R4 is selected from the group comprising, preferably consisting of, halogen and cyano;
R5 is C2-C6 alkyl;
R6 is selected from the group comprising, preferably consisting of, hydrogen, halogen, cyano, alkoxy, amino, alkylamino, dialkylamino;
R7 and R8 independently from each other are hydrogen or halogen;
A is selected from the group comprising, preferably consisting of, aryl and heteroaryl;
n is an integer from 0 to 1.

In accordance with a further particular embodiment, the present invention relates to compounds of general formula (I), supra, in which:

R1 is halogen;
R2 is halogen;
R3 is hydrogen;
R4 is halogen;
R5 is C2-C6 alkyl;
R6 is hydrogen;
R7 and R8 are hydrogen;
A is phenyl or pyridyl;
n is an integer from 0 to 1.

It is to be understood that the present invention relates to any sub-combination within any embodiment of the present invention of compounds of general formula (I), supra.

More particularly still, the present invention covers compounds of general formula (I) which are disclosed in the Example section of this text, infra.

Definitions

The term "alkoxy" denotes an alkyl group as defined herein attached via oxygen linkage to the rest of the molecule. Representative examples of those groups are methoxy and ethoxy.

The term "alkyl" refers to a straight or branched hydrocarbon chain radical consisting solely of carbon and hydrogen atoms, containing solely carbon and hydrogen atoms, containing no unsaturation, having from one to eight carbon atoms, and which is attached to the rest of the molecule by a single bond, such as illustratively, methyl, ethyl, n-propyl, 1-methylethyl (isopropyl), n-butyl, n-pentyl, and 1,1-dimethylethyl (t-butyl).

The term "alkylamino" is to be understood as preferably meaning an alkyl-amino group, meaning e.g. methylamino, ethylamino, propylamino, iso-propylamino, tert-butylamino.

The term "aryl" refers to aromatic radicals having in the range of 6 up to 14 carbon atoms such as phenyl, naphthyl, tetrahydronaphthyl, indanyl, biphenyl, preferably being phenyl.

The term "cycloalkyl" denotes a non-aromatic mono or multicyclic ring system of about 3 to 12 carbon atoms such as cyclopropyl, cyclobutyl, cyclopentyl, cyclohexyl and examples of multicyclic cycloalkyl groups include perhydronaphthyl, adamantyl and norbornyl groups bridged to a cyclic group or sprirobicyclic groups e.g spiro(4,4) non-2-yl.

The term "dialkylamino" is to be understood as preferably meaning a (alkyl)$_2$amino group, meaning e.g. dimethylamino, diethylamino, ethylmethylamino, diethylamino.

The term "halogen" refers to radicals of fluorine, chlorine, bromine and iodine.

As used herein, the term "heteroaryl" is understood as meaning an aromatic ring system which comprises 5-14 ring atoms, preferably 5 or 6 atoms, and which contains at least one heteroatom which may be identical or different, said heteroatom being such as nitrogen, NH, N-alkyl, oxygen, or sulphur, and can be monocyclic or bicyclic. Preferably, heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, etc., and benzo derivatives thereof, such as, e.g., benzofuranyl, benzothienyl, benzoxazolyl, benzimidazolyl, benzotriazolyl, indazolyl, indolyl, isoindolyl, etc.; or pyridyl, pyridazinyl, pyrimidinyl, pyrazinyl, triazinyl, etc., and benzo derivatives thereof, such as, for example, quinolinyl, isoquinolinyl, etc; preferably being indazolyl and pyridyl.

As used herein, the term "$C_2$-$C_6$" is to be understood as meaning an alkyl group having a finite number of carbon atoms of 2 to 6, i.e. 2, 3, 4, 5, or 6 carbon atoms. It is to be understood further that said term "$C_2$-$C_6$" is to be interpreted as any sub-range comprised therein, e.g. $C_2$-$C_6$, $C_2$-$C_5$, $C_3$-$C_4$, $C_2$-$C_3$; preferably $C_2$-$C_3$, $C_2$-$C_4$, $C_2$-$C_5$, $C_2$-$C_6$; more preferably $C_2$-$C_4$.

Where the plural form of the word compounds, salts, polymorphs, hydrates, solvates and the like, is used herein, this is taken to mean also a single compound, salt, polymorph, isomer, hydrate, solvate or the like.

The compounds of this invention may contain one or more asymmetric centers, depending upon the location and nature of the various substituents desired. Asymmetric carbon atoms may be present in the (R) or (S) configuration, resulting in racemic mixtures in the case of a single asymmetric center, and diastereomeric mixtures in the case of multiple asymmetric centers. In certain instances, asymmetry may also be present due to restricted rotation about a given bond, for example, the central bond adjoining two substituted aromatic rings of the specified compounds. Substituents on a ring may also be present in either cis or trans form. It is intended that all such configurations (including enantiomers and diastereomers), are included within the scope of the present invention. Preferred compounds are those which produce the more desirable biological activity. Separated, pure or partially purified isomers and stereoisomers or racemic or diastereomeric mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallization. The optically active bases or acids are then liberated from the separated diastereomeric salts. A different process for separation of optical isomers involves the use of chiral chromatography (e.g., chiral HPLC columns), with or without conventional derivitization, optimally chosen to maximize the separation of the enantiomers. Suitable chiral HPLC columns are manufactured by Diacel, e.g., Chiracel OD and Chiracel OJ among many others, all routinely selectable. Enzymatic separations, with or without derivitization, are also useful. The optically active compounds of this invention can likewise be obtained by chiral syntheses utilizing optically active starting materials.

The present invention also relates to useful forms of the compounds as disclosed herein, such as pharmaceutically acceptable salts, co-precipitates, metabolites, hydrates, solvates and prodrugs of all the compounds of examples. The term "pharmaceutically acceptable salt" refers to a relatively non-toxic, inorganic or organic acid addition salt of a compound of the present invention. For example, see S. M. Berge, et al. "Pharmaceutical Salts," *J. Pharm. Sci.* 1977, 66, 1-19. Pharmaceutically acceptable salts include those obtained by reacting the main compound, functioning as a base, with an inorganic or organic acid to form a salt, for example, salts of hydrochloric acid, sulfuric acid, phosphoric acid, methane sulfonic acid, camphor sulfonic acid, oxalic acid, maleic acid, succinic acid and citric acid. Pharmaceutically acceptable salts also include those in which the main compound functions as an acid and is reacted with an appropriate base to form, e.g., sodium, potassium, calcium, magnesium, ammonium, and chorine salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

Representative salts of the compounds of this invention include the conventional non-toxic salts and the quaternary ammonium salts which are formed, for example, from inorganic or organic acids or bases by means well known in the art. For example, such acid addition salts include acetate, adipate, alginate, ascorbate, aspartate, benzoate, benzenesulfonate, bisulfate, butyrate, citrate, camphorate, camphorsulfonate, cinnamate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, itaconate, lactate, maleate, mandelate, methanesulfonate, 2-naphthalenesulfonate, nicotinate, nitrate, oxalate, pamoate, pectinate, persulfate, 3-phenylpropionate, picrate, pivalate, propionate, succinate, sulfonate, tartrate, thiocyanate, tosylate, and undecanoate.

Base salts include alkali metal salts such as potassium and sodium salts, alkaline earth metal salts such as calcium and magnesium salts, and ammonium salts with organic bases such as dicyclohexylamine and N-methyl-D-glucamine. Additionally, basic nitrogen containing groups may be quaternized with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and strearyl chlorides, bromides and iodides, aralkyl halides like benzyl and phenethyl bromides and others.

A solvate for the purpose of this invention is a complex of a solvent and a compound of the invention in the solid state. Exemplary solvates would include, but are not limited to, complexes of a compound of the invention with ethanol or methanol. Hydrates are a specific form of solvate wherein the solvent is water.

Pharmaceutical Compositions of the Compounds of the Invention

This invention also relates to pharmaceutical compositions containing one or more compounds of the present invention. These compositions can be utilized to achieve the desired pharmacological effect by administration to a patient in need thereof. A patient, for the purpose of this invention, is a mammal, including a human, in need of treatment for the particular condition or disease. Therefore, the present invention includes pharmaceutical compositions that are comprised of a pharmaceutically acceptable carrier and a pharmaceutically effective amount of a compound, or salt thereof, of the present invention. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is preferably that amount which produces a result or exerts an influence on the particular condition being treated. The compounds of the present invention can be administered with pharmaceutically-acceptable carriers well known in the art using any effective conventional dosage unit forms, including immediate, slow and timed release preparations, orally, parenterally, topically, nasally, ophthalmically, optically, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatin type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatin, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, coloring agents, and flavoring agents such as peppermint, oil of wintergreen, or cherry flavoring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavoring and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavoring and coloring agents.

The compounds of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: Powell, M. F. et al, "Compendium of Excipients for Parenteral Formulations" *PDA Journal of Pharmaceutical Science & Technology* 1998, 52(5), 238-311; Strickley, R. G "Parenteral Formulations of Small Molecule Therapeutics Marketed in the United States (1999)-Part-1" *PDA Journal of Pharmaceutical Science & Technology* 1999, 53(6), 324-349; and Nema, S. et al, "Excipients and Their Use in Injectable Products" *PDA Journal of Pharmaceutical Science & Technology* 1997, 51(4), 166-171.

Commonly used pharmaceutical ingredients that can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

is aerosol propellants (examples include but are not limited to carbon dioxide, $CCl_2F_2$, $F_2ClC\text{—}CClF_2$ and $CClF_3$)

air displacement agents (examples include but are not limited to nitrogen and argon);

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate)

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection)

chelating agents (examples include but are not limited to edetate disodium and edetic acid)

colorants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate)

flavorants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:

Sterile IV Solution: A 5 mg/mL solution of the desired compound of this invention can be made using sterile, injectable water, and the pH is adjusted if necessary. The solution is diluted for administration to 1-2 mg/mL with sterile 5% dextrose and is administered as an IV infusion over about 60 minutes.

Lyophilized powder for IV administration: A sterile preparation can be prepared with (i) 100-1000 mg of the desired compound of this invention as a lypholized powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 minutes.

Intramuscular suspension: The following solution or suspension can be prepared, for intramuscular injection:

50 mg/mL of the desired, water-insoluble compound of this invention 5 mg/mL sodium carboxymethylcellulose 4 mg/mL TWEEN 80

9 mg/mL sodium chloride 9 mg/mL benzyl alcohol

Hard Shell Capsules: A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules: A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets: A large number of tablets are prepared by conventional procedures so that the dosage unit is 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules: These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Method of Treating Hyper-Proliferative Disorders

The present invention relates to a method for using the compounds of the present invention and compositions thereof, to treat mammalian hyper-proliferative disorders. Compounds can be utilized to inhibit, block, reduce, decrease, etc., cell proliferation and/or cell division, and/or produce apoptosis. This method comprises administering to a mammal in need thereof, including a human, an amount of a compound of this invention, or a pharmaceutically acceptable salt, isomer, polymorph, metabolite, hydrate, solvate or ester thereof; etc. which is effective to treat the disorder. Hyperproliferative disorders include but are not limited, e.g., psoriasis, keloids, and other hyperplasias affecting the skin, benign prostate hyperplasia (BPH), solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

Methods of Treating Kinase Disorders

The present invention also provides methods for the treatment of disorders associated with aberrant mitogen extracellular kinase activity, including, but not limited to stroke, heart failure, hepatomegaly, cardiomegaly, diabetes, Alzheimer's disease, cystic fibrosis, symptoms of xenograft rejections, septic shock or asthma.

Effective amounts of compounds of the present invention can be used to treat such disorders, including those diseases (e.g., cancer) mentioned in the Background section above. Nonetheless, such cancers and other diseases can be treated with compounds of the present invention, regardless of the mechanism of action and/or the relationship between the kinase and the disorder.

The phrase "aberrant kinase activity" or "aberrant tyrosine kinase activity," includes any abnormal expression or activity of the gene encoding the kinase or of the polypeptide it encodes. Examples of such aberrant activity, include, but are not limited to, over-expression of the gene or polypeptide; gene amplification; mutations which produce constitutively-active or hyperactive kinase activity; gene mutations, deletions, substitutions, additions, etc.

The present invention also provides for methods of inhibiting a kinase activity, especially of mitogen extracellular kinase, comprising administering an effective amount of a compound of the present invention, including salts, polymorphs, metabolites, hyrdates, solvates, prodrugs (e.g.: esters) thereof, and diastereoisomeric forms thereof. Kinase activity can be inhibited in cells (e.g., in vitro), or in the cells of a mammalian subject, especially a human patient in need of treatment.

Methods of Treating Angiogenic Disorders

The present invention also provides methods of treating disorders and diseases associated with excessive and/or abnormal angiogenesis.

Inappropriate and ectopic expression of angiogenesis can be deleterious to an organism. A number of pathological conditions are associated with the growth of extraneous blood vessels. These include, e.g., diabetic retinopathy, ischemic retinal-vein occlusion, and retinopathy of prematurity (Aiello et al. *New Engl. J. Med.* 1994, 331, 1480; Peer et al. *Lab. Invest.* 1995, 72, 638), age-related macular degeneration (AMD; see, Lopez et al. *Invest. Opththalmol. Vis. Sci.* 1996, 37, 855), neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumor enlargement and metastasis. Moreover, the growth of new blood and lymph vessels in a tumor provides an escape route for renegade cells, encouraging metastasis and the consequence spread of the cancer. Thus, compounds of the present invention can be utilized to treat and/or prevent any of the aforementioned angiogenesis disorders, e.g., by inhibiting and/or reducing blood vessel formation; by inhibiting, blocking, reducing, decreasing, etc. endothelial cell proliferation or other types involved in angiogenesis, as well as causing cell death or apoptosis of such cell types.

Dose and Administration

Based upon standard laboratory techniques known to evaluate compounds useful for the treatment of hyper-proliferative disorders and angiogenic disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Combination Therapies

The compounds of this invention can be administered as the sole pharmaceutical agent or in combination with one or more other pharmaceutical agents where the combination causes no unacceptable adverse effects. For example, the compounds of this invention can be combined with known anti-hyper-proliferative or other indication agents, and the like, as well as with admixtures and combinations thereof. Other indication agents include, but are not limited to, anti-angiogenic agents, mitotic inhibitors, alkylating agents, anti-metabolites, DNA-intercalating antibiotics, growth factor inhibitors, cell cycle inhibitors, enzyme inhibitors, toposisomerase inhibitors, biological response modifiers, or anti-hormones.

The additional pharmaceutical agent can be aldesleukin, alendronic acid, alfaferone, alitretinoin, allopurinol, aloprim, aloxi, altretamine, aminoglutethimide, amifostine, amrubicin, amsacrine, anastrozole, anzmet, aranesp, arglabin, arsenic trioxide, aromasin, 5-azacytidine, azathioprine, BCG or tice BCG, bestatin, betamethasone acetate, betamethasone sodium phosphate, bexarotene, bleomycin sulfate, broxuridine, bortezomib, busulfan, calcitonin, campath, capecitabine, carboplatin, casodex, cefesone, celmoleukin, cerubidine, chlorambucil, cisplatin, cladribine, cladribine, clodronic acid, cyclophosphamide, cytarabine, dacarbazine, dactinomycin, DaunoXome, decadron, decadron phosphate, delestrogen, denileukin diftitox, depomedrol, deslorelin, dexrazoxane, diethylstilbestrol, diflucan, docetaxel, doxifluridine, doxorubicin, dronabinol, DW-166HC, eligard, elitek, ellence, emend, epirubicin, epoetin alfa, epogen, eptaplatin, ergamisol, estrace, estradiol, estramustine phosphate sodium, ethinyl estradiol, ethyol, etidronic acid, etopophos, etoposide, fadrozole, farston, filgrastim, finasteride, fligrastim, floxuridine, fluconazole, fludarabine, 5-fluorodeoxyuridine monophosphate, 5-fluorouracil (5-FU), fluoxymesterone, flutamide, formestane, fosteabine, fotemustine, fulvestrant, gammagard, gemcitabine, gemtuzumab, gleevec, gliadel, goserelin, granisetron HCl, histrelin, hycamtin, hydrocortone, eyrthro-hydroxynonyladenine, hydroxyurea, ibritumomab tiuxetan, idarubicin, ifosfamide, interferon alpha, interferon-alpha 2, interferon alfa-2A, interferon alfa-2B, interferon alfa-n1, interferon alfa-n3, interferon beta, interferon gamma-1a, interleukin-2, intron A, iressa, irinotecan, kytril, lentinan sulphate, letrozole, leucovorin, leuprolide, leuprolide acetate, levamisole, levofolinic acid calcium salt, levothroid, levoxyl, lomustine, lonidamine, marinol, mechlorethamine, mecobalamin, medroxyprogesterone acetate, megestrol acetate, melphalan, menest, 6-mercaptopurine, Mesna, methotrexate, metvix, miltefosine, minocycline, mitomycin C, mitotane, mitoxantrone, Modrenal, Myocet, nedaplatin, neulasta, neumega, neupogen, nilutamide, nolvadex, NSC-631570, OCT-43, octreotide, ondansetron HCl, orapred, oxaliplatin, paclitaxel, pediapred, pegaspargase, Pegasys, pentostatin, picibanil, pilocarpine HCl, pirarubicin, plicamycin, porfimer sodium, prednimustine, prednisolone, prednisone, premarin, procarbazine, procrit, raltitrexed, rebif, rhenium-186 etidronate, rituximab, roferon-A, romurtide, salagen, sandostatin, sargramostim, semustine, sizofuran, sobuzoxane, solu-medrol, sparfosic acid, stem-cell therapy, streptozocin, strontium-89 chloride, synthroid, tamoxifen, tamsulosin, tasonermin, tastolactone, taxotere, teceleukin, temozolomide, teniposide, testosterone propionate, testred, thioguanine, thiotepa, thyrotropin, tiludronic acid, topotecan, toremifene, tositumomab, trastuzumab, treosulfan, tretinoin, trexall, trimethylmelamine, trimetrexate, triptorelin acetate, triptorelin pamoate, UFT, uridine, valrubicin, vesnarinone, vinblastine, vincristine, vindesine, vinorelbine, virulizin, zinecard, zinostatin stimalamer, zofran, ABI-007, acolbifene, actimmune, affinitak, aminopterin, arzoxifene, asoprisnil, atamestane, atrasentan, sorafenib, avastin, CCI-779, CDC-501, celebrex, cetuximab, crisnatol, cyproterone acetate, decitabine, DN-101, doxorubicin-MTC, dSLIM, dutasteride, edotecarin, eflornithine, exatecan, fenretinide, histamine dihydrochloride, histrelin hydrogel implant, holmium-166 DOTMP, ibandronic acid, interferon gamma, intron-PEG, ixabepilone, keyhole limpet hemocyanin, L-651582, lanreotide, lasofoxifene, libra, lonafarnib, miproxifene, minodronate, MS-209, liposomal MTP-PE, MX-6, nafarelin, nemorubicin, neovastat, nolatrexed, oblimersen, onco-TCS, osidem, paclitaxel polyglutamate, pamidronate disodium, PN-401, QS-21, quazepam, R-1549, raloxifene, ranpirnase, 13-cis-retinoic acid, satraplatin, seocalcitol, T-138067, tarceva, taxoprexin, thymosin alpha 1, tiazofurine, tipifarnib, tirapazamine, TLK-286, toremifene, TransMID-107R, valspodar, vapreotide, vatalanib, verteporfin, vinflunine, Z-100, zoledronic acid or combinations thereof.

Optional anti-hyper-proliferative agents which can be added to the composition include but are not limited to compounds listed on the cancer chemotherapy drug regimens in the 11$^{th}$ Edition of the *Merck Index*, (1996), which is hereby incorporated by reference, such as asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Other anti-hyper-proliferative agents suitable for use with the composition of the invention include but are not limited to those compounds acknowledged to be used in the treatment of neoplastic diseases in *Goodman and Gilman's The Pharmacological Basis of Therapeutics* (Ninth Edition), editor Molinoff et al., publ. by McGraw-Hill, pages 1225-1287, (1996), which is hereby incorporated by reference, such as aminoglutethimide, L-asparaginase, azathioprine, 5-azacytidine cladribine, busulfan, diethylstilbestrol, 2',2'-difluorodeoxycytidine, docetaxel, erythrohydroxynonyl adenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethyl-melamine, uridine, and vinorelbine.

Other anti-hyper-proliferative agents suitable for use with the composition of the invention include but are not limited to other anti-cancer agents such as epothilone and its derivatives, irinotecan, raloxifen and topotecan.

The compounds of the invention may also be administered in combination with protein therapeutics. Such protein therapeutics suitable for the treatment of cancer or other angiogenic disorders and for use with the compositions of the invention include, but are not limited to, an interferon (e.g., interferon .alpha., .beta., or .gamma.) supraagonistic monoclonal antibodies, Tuebingen, TRP-1 protein vaccine, Colostrinin, anti-FAP antibody, YH-16, gemtuzumab, infliximab, cetuximab, trastuzumab, denileukin diftitox, rituximab, thymosin alpha 1, bevacizumab, mecasermin, mecasermin rinfabate, oprelvekin, natalizumab, rhMBL, MFE-CP1+ZD-2767-P, ABT-828, ErbB2-specific immunotoxin, SGN-35, MT-103, rinfabate, AS-1402, B43-genistein, L-19 based radioimmunotherapeutics, AC-9301, NY-ESO-1 vaccine, IMC-1C11, CT-322, rhCC10, r(m)CRP, MORAb-009, aviscumine, MDX-1307, Her-2 vaccine, APC-8024, NGR-hTNF, rhH1.3, IGN-311, Endostatin, volociximab, PRO-1762, lexatumumab, SGN-40, pertuzumab, EMD-273063, L19-IL-2 fusion protein, PRX-321, CNTO-328, MDX-214, tigapotide, CAT-3888, labetuzumab, alpha-particle-emitting radioisotope-llinked lintuzumab, EM-1421, HyperAcute vaccine, tucotuzumab celmoleukin, galiximab, HPV-16-E7, Javelin—prostate cancer, Javelin—melanoma, NY-ESO-1 vaccine, EGF vaccine, CYT-004-MelQbG10, WT1 peptide, oregovomab, ofatumumab, zalutumumab, cintredekin besudotox, WX-G250, Albuferon, aflibercept, denosumab, vaccine, CTP-37, efungumab, or 131I-chTNT-1/B. Monoclonal antibodies useful as the protein therapeutic include, but are not limited to, muromonab-CD3, abciximab, edrecolomab, daclizumab, gentuzumab, alemtuzumab, ibritumomab, cetuximab, bevicizumab, efalizumab, adalimumab, omalizumab, muromomab-CD3, rituximab, daclizumab, trastuzumab, palivizumab, basiliximab, and infliximab.

Generally, the use of cytotoxic and/or cytostatic agents in combination with a compound or composition of the present invention will serve to:

(1) yield better efficacy in reducing the growth of a tumor or even eliminate the tumor as compared to administration of either agent alone,
(2) provide for the administration of lesser amounts of the administered chemo-therapeutic agents,
(3) provide for a chemotherapeutic treatment that is well tolerated in the patient with fewer deleterious pharmacological complications than observed with single agent chemotherapies and certain other combined therapies,
(4) provide for treating a broader spectrum of different cancer types in mammals, especially humans,
(5) provide for a higher response rate among treated patients,
(6) provide for a longer survival time among treated patients compared to standard chemotherapy treatments,
(7) provide a longer time for tumor progression, and/or
(8) yield efficacy and tolerability results at least as good as those of the agents used alone, compared to known instances where other cancer agent combinations produce antagonistic effects.

Methods of Sensitizing Cells to Radiation

In a distinct embodiment of the present invention, a compound of the present invention may be used to sensitize a cell to radiation. That is, treatment of a cell with a compound of the present invention prior to radiation treatment of the cell renders the cell more susceptible to DNA damage and cell death than the cell would be in the absence of any treatment with a compound of the invention. In one aspect, the cell is treated with at least one compound of the invention.

Thus, the present invention also provides a method of killing a cell, wherein a cell is administered one or more compounds of the invention in combination with conventional radiation therapy.

The present invention also provides a method of rendering a cell more susceptible to cell death, wherein the cell is treated one or more compounds of the invention prior to the treatment of the cell to cause or induce cell death. In one aspect, after the cell is treated with one or more compounds of the invention, the cell is treated with at least one compound, or at least one method, or a combination thereof, in order to cause DNA damage for the purpose of inhibiting the function of the normal cell or killing the cell.

In one embodiment, a cell is killed by treating the cell with at least one DNA damaging agent. That is, after treating a cell with one or more compounds of the invention to sensitize the cell to cell death, the cell is treated with at least one DNA damaging agent to kill the cell. DNA damaging agents useful in the present invention include, but are not limited to, chemotherapeutic agents (eg., cisplatinum), ionizing radiation (X-rays, ultraviolet radiation), carcinogenic agents, and mutagenic agents.

In another embodiment, a cell is killed by treating the cell with at least one method to cause or induce DNA damage. Such methods include, but are not limited to, activation of a cell signaling pathway that results in DNA damage when the pathway is activated, inhibiting of a cell signaling pathway that results in DNA damage when the pathway is inhibited, and inducing a biochemical change in a cell, wherein the change results in DNA damage. By way of a non-limiting example, a DNA repair pathway in a cell can be inhibited, thereby preventing the repair of DNA damage and resulting in an abnormal accumulation of DNA damage in a cell.

In one aspect of the invention, a compound of the invention is administered to a cell prior to the radiation or orther induction of DNA damage in the cell. In another aspect of the invention, a compound of the invention is administered to a cell concomitantly with the radiation or orther induction of DNA damage in the cell. In yet another aspect of the invention, a compound of the invention is administered to a cell immediately after radiation or orther induction of DNA damage in the cell has begun.

In another aspect, the cell is in vitro. In another embodiment, the cell is in vivo.

In accordance with another aspect, the present invention covers a method of preparing compounds of the present invention, the method comprising the steps as described herein.

Method(s) of Making the Compounds of the Invention
General Preparative Methods

The particular process to be utilized in the preparation of the compounds used in this embodiment of the invention depends upon the specific compound desired. Such factors as the selection of the specific substituents play a role in the path to be followed in the preparation of the specific compounds of this invention. Those factors are readily recognized by one of ordinary skill in the art.

The compounds of the invention may be prepared by use of known chemical reactions and procedures. Nevertheless, the following general preparative methods are presented to aid the reader in synthesizing the compounds of the present invention, with more detailed particular examples being presented below in the experimental section describing the working examples.

The compounds of the invention can be made according to conventional chemical methods, and/or as disclosed below, from starting materials which are either commercially available or producible according to routine, conventional chemical methods. General methods for the preparation of the compounds are given below, and the preparation of representative compounds is specifically illustrated in examples.

Synthetic transformations that may be employed in the synthesis of compounds of this invention and in the synthesis of intermediates involved in the synthesis of compounds of this invention are known by or accessible to one skilled in the art. Collections of synthetic transformations may be found in compilations, such as:

J. March. *Advanced Organic Chemistry*, 4th ed.; John Wiley: New York (1992)

R. C. Larock. *Comprehensive Organic Transformations*, 2nd ed.; Wiley-VCH: New York (1999)

F. A. Carey; R. J. Sundberg. *Advanced Organic Chemistry*, 2nd ed.; Plenum Press: New York (1984)

T. W. Greene; P. G. M. Wuts. *Protective Groups in Organic Synthesis*, 3rd ed.; John Wiley: New York (1999)

L. S. Hegedus. *Transition Metals in the Synthesis of Complex Organic Molecules*, 2nd ed.; University Science Books: Mill Valley, Calif. (1994)

L. A. Paquette, Ed. *The Encyclopedia of Reagents for Organic Synthesis*; John Wiley: New York (1994)

A. R. Katritzky; O. Meth-Cohn; C. W. Rees, Eds. *Comprehensive Organic Functional Group Transformations*; Pergamon Press: Oxford, UK (1995)

G. Wilkinson; F. G. A. Stone; E. W. Abel, Eds. *Comprehensive Organometallic Chemistry*; Pergamon Press: Oxford, UK (1982)

B. M. Trost; I. Fleming. *Comprehensive Organic Synthesis*; Pergamon Press: Oxford, UK (1991)

A. R. Katritzky; C. W. Rees Eds. *Comprehensive Heterocylic Chemistry*; Pergamon Press: Oxford, UK (1984)

A. R. Katritzky; C. W. Rees; E. F. V. Scriven, Eds. *Comprehensive Heterocylic Chemistry II*; Pergamon Press: Oxford, UK (1996)

C. Hansch; P. G. Sammes; J. B. Taylor, Eds. *Comprehensive Medicinal Chemistry*; Pergamon Press: Oxford, UK (1990).

In addition, recurring reviews of synthetic methodology and related topics include *Organic Reactions*; John Wiley: New York; *Organic Syntheses*; John Wiley: New York; *Reagents for Organic Synthesis*: John Wiley: New York; *The Total Synthesis of Natural Products*; John Wiley: New York; *The Organic Chemistry of Drug Synthesis*; John Wiley: New York; *Annual Reports in Organic Synthesis*; Academic Press: San Diego Calif.; and *Methoden der Organischen Chemie* (Houben-Weyl); Thieme: Stuttgart, Germany. Furthermore, databases of synthetic transformations include Chemical Abstracts, which may be searched using either CAS OnLine or SciFinder, *Handbuch der Organischen Chemie* (Beilstein), which may be searched using SpotFire, and REACCS.

Reaction Schemes:

The following schemes illustrate general synthetic routes to the compounds of general formula (I) of the invention and are not intended to be limiting. It needs to be understood that transformations generically described in the following paragraphs may be performed at different reaction temperatures and in different solvents depending upon, for example, the reactivity of reagents and their respective solubility characteristics. More specifically, certain transformations may require heating in a solvent of a suitable boiling point. In specific cases heating of reaction mixtures may be achieved by using a microwave oven. In certain cases additives such as, for example, bases, phase transfer catalysts or ionic liquids may be used to modify reaction conditions to improve reaction turnover oder heating characteristics. It is obvious to the person skilled in the art that the order of transformations as exemplified in Schemes 1 to 4 can be modified in various ways. The order of transformations exemplified in Schemes 1 to 4 is therefore not intended to be limiting. In addition, interconversion of substituents, for example of residues R1, R2, R3, R4, R5, R6, R7 or R8 can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis*, $3^{rd}$ edition, Wiley 1999). Some transformations described below may give rise to mixtures of regioisomers, for example, transformations illustrated in Scheme 1 and 2. Separation of these regioisomers may be achieved by various methods, including, for example, column chromatography, crystallization or preparative HPLC.

Reaction Scheme 1 illustrates one general method for the preparation of the compounds of the present invention of Formula (I).

Reaction Scheme 1

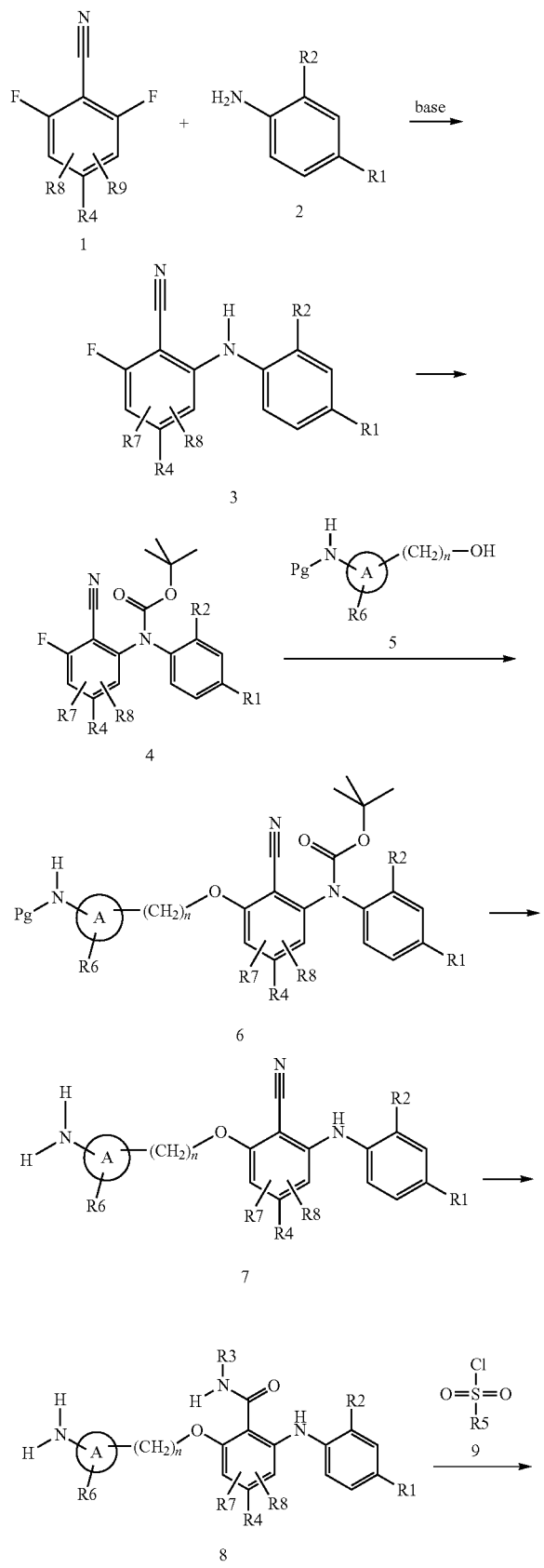

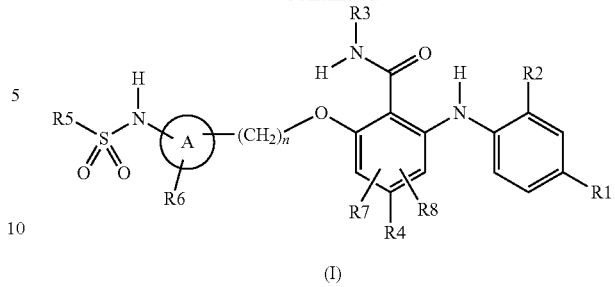

(I)

Scheme 1 General procedure for the preparation of compounds of the general Formula (I), wherein R1, R2, R3, R4, R5, R6, R7, R8, n and A are as defined in the description and claims of this invention and Pg stands for a suitable protecting group as described in the subsequent paragraphs, such as, for example, a tert-butoxycarbonyl group.

A 2,6-difluoro benzonitrile of Formula 1 is reacted with an aniline of Formula 2 in the presence of a suitable base, such as for example potassium tert-butoxide or lithium hexamethyldisilazide (LiHMDS), to form an amine of Formula 3. This amine is then transformed into its tert-butoxycarbonyl (Boc) derivative 4 by reaction with $Boc_2O$ in the presence of a suitable base. Alternatively, other suitable protecting groups are a benzyloxy carbonyl group or derivatives thereof. Appropriate protecting group reagents and their introduction are well-known to the person skilled in the art (see for example T. W. Greene and P. G. M. Wuts in *Protective Groups in Organic Synthesis*, 3$^{rd}$ edition, Wiley 1999). Subsequently the intermediate 4 is reacted with an alcohol of Formula 5 (which comprises an amine functionality optionally suitably protected for such a transformation with a protecting group Pg) in the presence of a suitable base, such as for example cesium carbonate, sodium hydride or potassium tert-butoxide, to form an ether of Formula 6. Suitable protecting groups (Pg) for the amine group in compounds of Formula 5 are, for example, tert-butoxy carbonyl (Boc), benzyloxy carbonyl, acetyl or pivaloyl. The amine group in compounds of Formula 5 may alternatively be protected in form of a phthalic imide or in form of a suitable imine. Alternatively, this amine group may be unprotected or be replaced by a nitro group for the substitution reaction which subsequently can be reduced to the amine under standard nitro reduction conditions, such as, for example, hydrogenation in the presence of a suitable transition metal catalyst, or reaction with a reducing agent such as, for example, $SnCl_2$, $TiCl_3$ or Fe.

Compound 6 is then liberated from its protecting groups in a concerted or stepwise fashion using standard conditions as known to the person skilled in the art to form an amine of Formula 7. These standard conditions include, but are not limited to, treatment with an acid, such as, for example, hydrochloric acid or trifluoro acetic acid, treatment with a Lewis acid, such as, for example, $AlCl_3$, or treatment with a base, such as, for example, sodium hydroxide, sodium ethanolate, lithium hydroxide, hydrazine or methyl hydrazine. Reduction of a nitrile of formula 7 by reaction with, for example, $H_2O_2$ in the presence of NaOH, gives rise to amides of formula 8 (R3=H), which are optionally subsequently alkylated to give amides of formula 8 with R3≠H. Finally, coupling with alkyl sulfonyl chlorides of general Formula 9 provides the compounds of the present invention of Formula (I).

In a modified route to compounds of the present invention, starting material 1 may already contain a suitable amide group in place of the nitrile group thereby allowing to dispense the nitrile reduction step (7►8 in Scheme 1). As a further alternative, the amide functionality in starting material 1 may be replaced by a carboxylic acid group which is then transformed into an amide in a subsequent transformations by reaction with, for example, ammonia or an appropriately substituted amine in the presence of a coupling agents such as, for example, carbonyl diimidazolide (CDI) or T3P. Furthermore, protection of the biaryl amine position with, for example, a tert-butoxycarbonyl group, may not be necessary, thereby allowing to dispense the protection step (3►4 in Scheme 1) and the subsequent deprotection.

Scheme 2 outlines an alternative route for the preparation of compounds of the present invention of Formula (I).

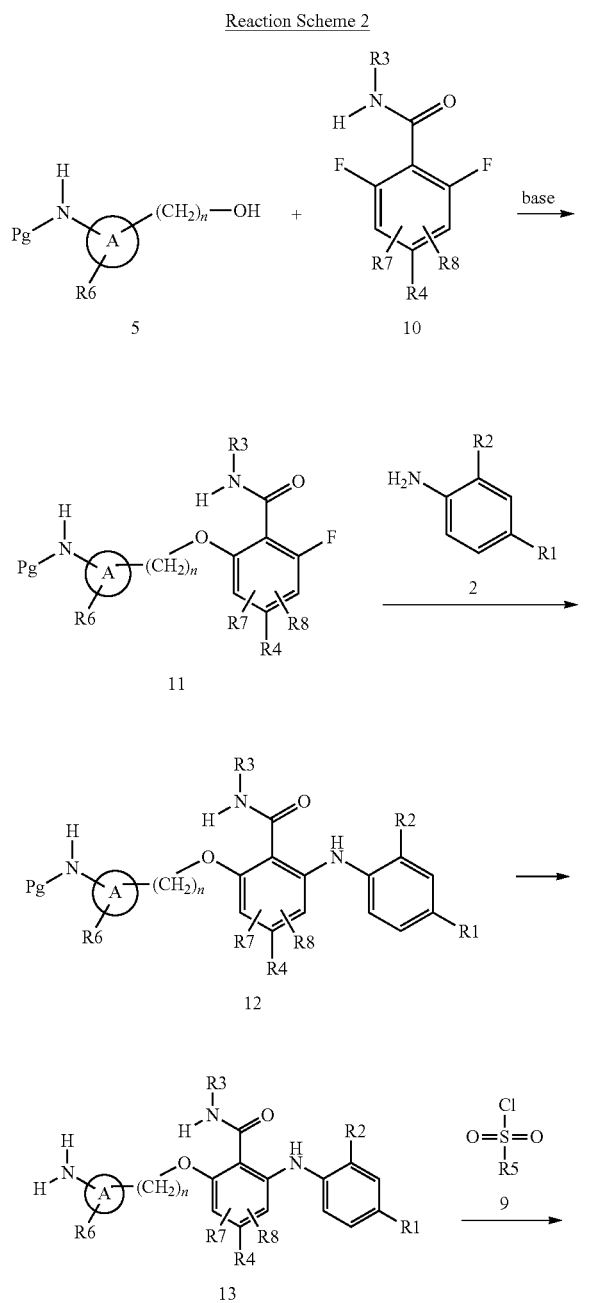

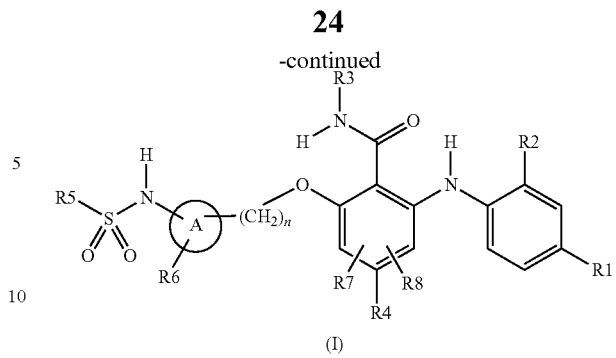

Scheme 2 Further general procedure for the preparation of compounds of the general Formula (I), wherein R1, R2, R3, R4, R5, R6, R7, R8, n and A are as defined in the description and claims of this invention and Pg stands for a suitable protecting group as described in the subsequent paragraphs, such as, for example, a tert-butoxycarbonyl group.

A 2,6-difluorophenyl derivative of Formula 10 is reacted in the presence of a suitable base, such as, for example, sodium hydride, with an alcohol of formula 5 (which comprises an amine functionality suitably protected with a Pg group for such a transformation) to form an ether of Formula 11. Suitable protecting groups for the amine group in compounds of Formula 5 are, for example, tert-butoxy carbonyl (Boc), benzyloxy carbonyl, acetyl or pivaloyl or alternatives as described above. The ether of Formula 11 is then reacted with anilines of Formula 2 in the presence of a suitable base to give amines of general formula 12. Subsequently, removal of the Pg group under conditions as described above yields compounds of Formula 13, which are then transformed into compounds of the invention of Formula (I) as described above.

As a further alternative, the amide functionality in starting material 10 may be replaced by a carboxylic acid group which is then transformed into an amide in a subsequent transformations by reaction with, for example, ammonia or an appropriately substituted amine in the presence of a coupling agents such as, for example, carbonyl diimidazolide (CDI) or T3P.

Alternatively, the amide functionality in starting material 10 may be replaced by a nitrile which is then transformed into an amide in a subsequent transformations under conditions as described above (see Scheme 3).

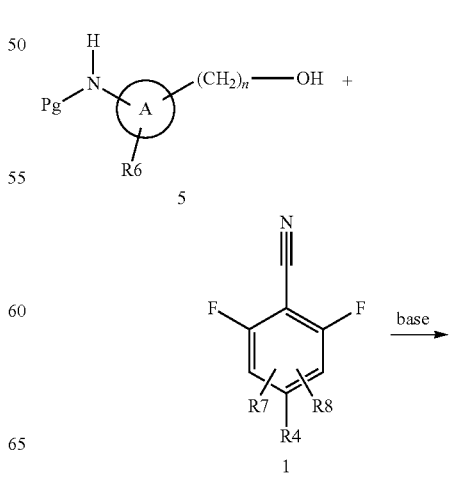

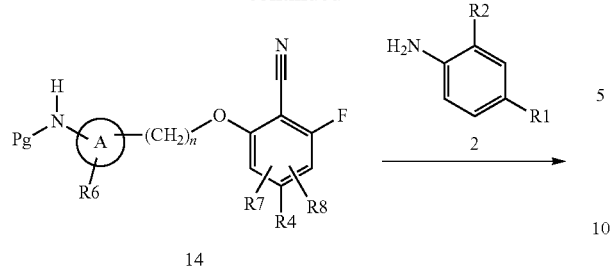

14

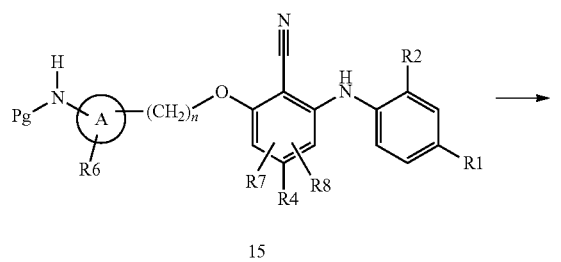

15

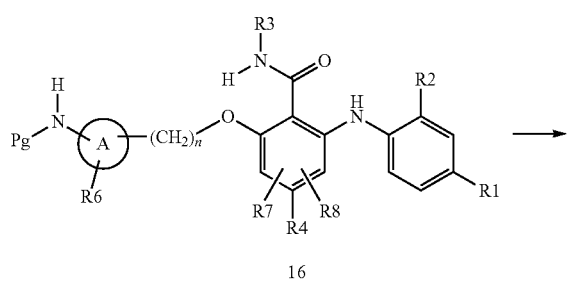

16

Scheme 3 Further general procedure for the preparation of compounds of the general Formula (I), wherein R1, R2, R3, R4, R5, R7, R8, R9, A and n are as defined in the description and claims of this invention and Pg stands for a suitable protecting group as described in the subsequent paragraphs, such as, for example, a tert-butoxycarbonyl group.

Nucleophilic reaction of a benzonitrile of Formula 1 with a phenol of formula 5 (optionally carrying a suitable protection group Pg as described above) provides ethers of formula 14. Under appropriate conditions this protection group Pg can be omitted. Subsequent nucleophilic displacement with anilines of Formula 2 to biaryl amines of Formula 15 is followed by nitrile hydrolysis to amides of Formula 16 under conditions as described above. Deprotection leads to amines of formula 13 which are then transformed into compounds of the present invention as described above.

Reaction Scheme 4 illustrates one more specific general method for the preparation of the formula (Ib) compounds [Formula (I) where R1=ethinyl].

Reaction Scheme 4

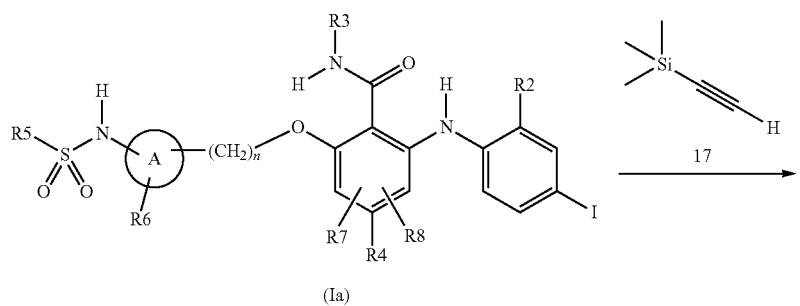

(Ia)

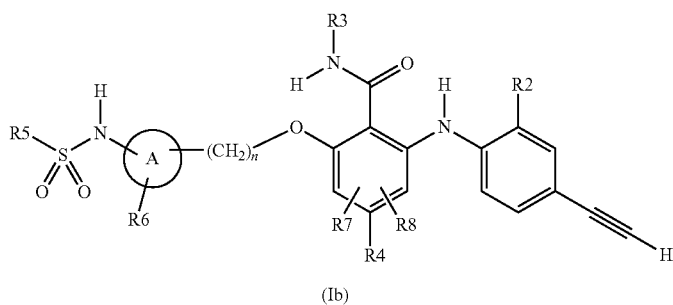

(Ib)

Scheme 4 Further general procedure for the preparation of compounds of the general Formula (Ib), wherein R2, R3, R4, R5, R6, R7, R8, n and A are as defined in the description and claims of this invention.

An intermediate of Formula (Ia) [Formula (I) where R1=iodo], prepared as described in Schemes 1 or 2, is reacted with trimethylsilylacetylene in a Sonogashira-type coupling reaction in the presence of catalytic amounts of a Pd catalyst, such as, for example, $PdCl_2(PPh_3)_2$ and catalytic amounts of copper iodide, in the presence of a suitable base followed by cleavage of the trimethylsilyl group by reaction with, for example, tetrabutylammonium fluoride or HCl or $K_2CO_3$/MeOH, to form the corresponding alkyne derivative of Formula Ib [Formula (I) where R1=ethinyl]. Alternatively, by using tetrabutylammonium fluoride as base in the Sonogashira-type coupling, coupling of TMS acetylene and cleavage of the TMS-group can be achieved in a one pot transformation. Transition metal-catalyzed couplings of (hetero)aryl halides with alkynes and trialkylsilyl alkynes are well known to the person skilled in the art (see for example (a) Chinchilla, R.; Najera, C. *Chem. Rev.* 2007, 107, 874; (b) Negishi, E.-i., Anastasia, L. *Chem. Rev.* 2003, 103, 1979; see also: (c) *Eur. J. Org. Chem.* 2005, 20, 4256; (d) *J. Org. Chem.* 2006, 71, 2535 and references therein; (e) *Chem. Commun.* 2004, 17, 1934). Various palladium-catalyst/co-catalyst/ligand/base/solvent combinations have been published in the scientific literature which allow a fine-tuning of the required reaction conditions in order to allow for a broad set of additional functional groups on both coupling partners (see references in the above cited reviews). Additionally, recently developed procedures employing e.g. zinc acetylides, alkynyl magnesium salts or alkynyl trifluoroborate salts further broaden the scope of this process. Instead of the iodo starting material (Ia) the corresponding bromo or chloro derivatives may be used. Introduction of an acetylene group as R1 group starting from the corresponding halide employing the described Sonogashira conditions may alternatively be achieved on an appropriate intermediate compounds (see Scheme 1 or Scheme 2 with R1 being iodo or bromo for appropriate intermediates).

EXPERIMENTAL DETAILS AND GENERAL PROCESSES

Abbreviations and Acronyms

A comprehensive list of the abbreviations used by organic chemists of ordinary skill in the art appears in The ACS Style Guide (third edition) or the Guidelines for Authors for the *Journal of Organic Chemistry*. The abbreviations contained in said lists, and all abbreviations utilized by organic chemists of ordinary skill in the art are hereby incorporated by reference. For purposes of this invention, the chemical elements are identified in accordance with the Periodic Table of the Elements, CAS version, Handbook of Chemistry and Physics, 67th Ed., 1986-87.

More specifically, when the following abbreviations are used throughout this disclosure, they have the following meanings:
$Ac_2O$ acetic anhydride
ACN acetonitrile
AcO (or OAc) acetate
anhyd anhydrous
aq aqueous
Ar aryl
atm atmosphere
ATP adenosine triphosphate
b.i.d. twice a day
Biotage silica gel chromatographic system, Biotage Inc.
Bn benzyl
bp boiling point
Bz benzoyl
BOC tert-butoxycarbonyl
n-BuOH n-butanol
t-BuOH tert-butanol
t-BuOK potassium tert-butoxide
calcd calculated
Cbz carbobenzyloxy
CDI carbonyl diimidazole
$CD_3OD$ methanol-$d_4$
Celite® diatomaceous earth filter agent, Celite Corp.
CI-MS chemical ionization mass spectroscopy
$^{13}C$ NMR carbon-13 nuclear magnetic resonance
conc concentrated
DCC dicyclohexylcarbodiimide
DCE dichloroethane
DCM dichloromethane
dec decomposition
DIBAL diisobutylaluminum hydroxide
DMAP 4-(N,N-dimethylamino)pyidine
DME 1,2-dimethoxyethane
DMF N,N-dimethylformamide
DMSO dimethylsulfoxide
DTT dithiothreitol
E entgegen (configuration)
e.g. for example
EI electron impact
ELSD evaporative light scattering detector
eq equivalent
ERK extracellular signal-regulated kinase
ESI electrospray ionisation
ES-MS electrospray mass spectroscopy
et al. and others
EtOAc ethyl acetate
EtOH ethanol (100%)
EtSH ethanethiol
$Et_2O$ diethyl ether
$Et_3N$ triethylamine
GC gas chromatography
GC-MS gas chromatography-mass spectroscopy
h hour, hours
$^1H$ NMR proton nuclear magnetic resonance
HCl hydrochloric acid
HEPES 4-(2-hydroxyethyl)-1-piperazineethanesulfonic acid
Hex hexane
HMPA hexamethylphosphoramide
HMPT hexamethylphosphoric triamide
HPLC high performance liquid chromatography
$IC_{50}$ drug concentration required for 50% inhibition
i.e. that is
insol insoluble
IPA isopropylamine
IR infrared
J coupling constant (NMR spectroscopy)
LAH lithium aluminum hydride
LC liquid chromatography
LC-MS liquid chromatography-mass spectrometry
LDA lithium diisopropylamide
MAPK mitogen-activated protein kinase
MeCN acetonitrile
MEK MAPK/ERK kinase
MHz megahertz
min minute, minutes
µL microliter
mL milliliter
µM micromolar mp melting point
MS mass spectrum, mass spectrometry
Ms methanesulfonyl
m/z mass-to-charge ratio
NBS N-bromosuccinimide
nM nanomolar
NMM 4-methylmorpholine
obsd observed
p page
PBS phosphate buffered saline
pp pages
PdCl$_2$dppf [1,1'-bis(diphenylphosphino)ferrocene]dichloropalladium(II)
Pd(OAc)$_2$ palladium acetate
pH negative logarithm of hydrogen ion concentration
pK negative logarithm of equilibrium constant
pK$_a$ negative logarithm of equilibrium constant for association
PS-DIEA polystyrene-bound diisopropylethylamine
q quartet (nmr)
qt quintet (nmr)
R$_f$ retention factor (TLC)
RT retention time (HPLC)
rt room temperature
TBAF tetra-n-butylammonium fluoride
TBST tris buffered saline with tween
TEA triethylamine
THF tetrahydrofuran
TFA trifluoroacetic acid
TFFH fluoro-N,N,N',N'-tetramethylformamidinium hexafluorophosphate
TLC thin layer chromatography
TMAD N,N,N',N'-tetramethylethylenediamine
TMSCl trimethylsilyl chloride
Ts p-toluenesulfonyl
v/v volume per volume
w/v weight per volume
w/w weight per weight
Z zusammen (configuration)

NMR peak forms in the following experimental section are stated as they appear in the spectra, possible higher order effects have not been considered. Chemical names were generated using AutoNom2000 as implemented in MDL ISIS Draw. In some cases generally accepted names of commercially available reagents were used in place of AutoNom2000 generated names. Reactions employing microwave irradiation may be run with a Biotage Initator® microwave oven optionally equipped with a robotic unit. The reported reaction times employing microwave heating are intended to be understood as fixed reaction times after reaching the indicated reaction temperature. The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. from Separtis such as Isolute® Flash silica gel or Isolute® Flash NH$_2$ silica gel in combination with a Flashmaster II autopurifier (Argonaut/Biotage) and eluents such as gradients of hexane/ethyl acetate or DCM/ethanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid or aqueous ammonia. In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc) of a compound of the present invention as isolated as described herein is not necessarily the only form in which said compound can be applied to a biological assay in order to quantify the specific biological activity.

The percentage yields reported in the following examples are based on the starting component that was used in the lowest molar amount. Air and moisture sensitive liquids and solutions were transferred via syringe or cannula, and introduced into reaction vessels through rubber septa. Commercial grade reagents and solvents were used without further purification. The term "concentrated under reduced pressure" refers to use of a Buchi rotary evaporator at a minimum pressure of approximately 15 mm of Hg. All temperatures are reported uncorrected in degrees Celsius (° C.).

In order that this invention may be better understood, the following examples are set forth. These examples are for the purpose of illustration only, and are not to be construed as limiting the scope of the invention in any manner. All publications mentioned herein are incorporated by reference in their entirety.

General Procedures

In the subsequent paragraphs detailed general procedures for the synthesis of key intermediates and compounds of the present invention are described.

General Procedure 1 (GP 1): Introduction of C2 Side Chain 1 eq of the 2-fluorophenyl substrate and 1.5 eq. of the 2,4-disubstituted benzenamine was dissolved in dry THF. Upon cooling to −60° C., 2-3 eq. of potassium tert-butoxide were added and the mixture was stirred for 30 min at this temperature. The mixture was allowed to warm to rt and was stirred until complete consumption of the starting material. The mixture was then concentrated to afford the crude product which was optionally further purified by flash column chromatography, trituration or preparative HPLC purification.

General Procedure 2 (GP 2): BOC Protection of the Diphenyl Amine

The diphenyl amine derivative (1 eq.) was dissolved in THF under Argon and DMAP (0.28 eq.) as well as di-tert-butyldicarbonate (1.56 eq.) were added. The mixture was stirred at rt until TLC or LCMS analysis showed final turnover. The mixture was concentrated to afford the crude target compound, which was optionally further purified by flash column chromatography, trituration or preparative HPLC purification.

General Procedure 3a (GP 3a): Introduction of C6 Side Chain (Conditions A)

The respective 6 fluoro benzene was dissolved in THF and an alcohol was added. The mixture was treated with sodium hydride (2.01 eq.) and stirred at rt for 48 h. The reaction mixture was poured onto ice water and extracted three times with ethyl acetate. The combined organic layers were washed one time with brine, dryed over sodium sulfate, filtered off and concentrated to afford the crude product which was optionally further purified by flash column chromatography, trituration or preparative HPLC purification.

General Procedure 3b (GP 3b): Introduction of C6 Side Chain (Conditions B)

The respective 6 fluoro benzene was dissolved in DMF, cesium carbonate (1-4 eq.) was added and the mixture allowed to stir at RT for 30 Min. Then an alcohol was added in DMF. The mixture was stirred in a sealed preassure tube for 2-48 h. Extractive work-up, combination of the organic layers and concentration in vacuo yielded the crude product which was optionally further purified by flash column chromatography, trituration or preparative HPLC purification.

General Procedure 3c (GP 3c): Introduction of C6 side chain (Conditions C)

The respective 6 fluoro benzene was dissolved in THF, KtOBu (1-2 eq.) was added and the mixture allowed to stir at RT for 30 Min. Then a solution of an alcohol in DMF was added. The mixture was stirred at 70° C. for 1-24 h. The mixture was partitioned between half concentrated brine and ethyl acetate and extracted twice with ethyl acetate. The combined organic layers were dryed over sodium sulphate, filtered off and concentrated to afford the crude product which was optionally further purified by flash column chromatography, trituration or preparative HPLC purification.

General Procedure 4 (GP 4): Clevage of Boc protecting group(s).

1 eq. of the Boc-protected substrate was suspended in dichloromethane and treated with excess TFA (5-20 eq.). The mixture was subsequently stirred at rt until complete consumption of the starting material. The reaction mixture was concentrated, redissolved in dichloromethane and sodium hydroxide solution (1M, aq.) was added. After phase separation the organic phase was concentrated to afford the crude product which was optionally further purified by flash column chromatography, trituration or preparative HPLC purification.

General Procedure 5 (GP 5): Hydrolysis of the Benzonitrile

The benzonitrile was dissolved in DMSO and 3 M aq. sodium hydroxide solution (1,1 eq) was added. The mixture was heated to 60-65° C. and hydrogen peroxide solution (aq., 30%, 10-80 eq.) was added slowly. The mixture was stirred for another 2 h at 65° C. (bath temp.) and then at rt until TLC or LCMS analysis showed no more turnover. The reaction mixture was poured onto ice water and extracted three times with ethyl acetate. The organic layer was washed one time with brine, dryed over sodium sulfate, filtered off and concentrated to afford the crude product which was optionally further purified by flash column chromatography, trituration or preparative HPLC purification.

General Procedure 6a (GP 6a): Preparation of Sulfonamides (Conditions A)

The respective amine (1 eq.) was dissolved in THF and treated with triethylamine (1.5 eq.) and the respective sulfonyl chloride (1.5 eq.). The reaction mixture was stirred at rt overnight, diluted with ethyl acetate, washed with saturated NaHCO$_3$ solution, dried and concentrated in vacuo. HPLC purification of the residue provided the desired compound.

General Procedure 6b (GP 6b): Preparation of Sulfonamides (Conditions B)

The respective amino compound (1 eq.) was dissolved in pyridine and treated with the respective sulfonyl chloride (1.2 eq., dissolved in pyridine). The reaction mixture was stirred at rt overnight. In case of incomplete turnover (based on TLC or LCMS analysis) the mixture was treated with additional sulfonylchloride (in pyridine) and stirring at rt was continued. After final turnover, the mixture was diluted with ethyl acetate, washed with water and the organic layers dried. Concentration in vacuo followed by flash column chromatography or HPLC purification provided the target compound.

General Procedure 7a (GP 7a): Sonogashira Coupling (Conditions A)

The respective iodo-aniline intermediate (1 eq.), bis[(1,2,4,5-eta)-1,5-diphenyl-1,4-pentadien-3-one]-palladium (0.004 eq.), copper(I) iodide (0.004 eq.) and triphenyl-phosphine (0.2 eq.) were weighed into a preassure tube and triethyl amine was added. Upon flushing three times with N$_2$, trimethylsilyl acetylene (6 eq.) was added, the preassure tube was sealed and the resulting suspension was stirred vigorously at 60° C. for 3 h. The mixture was concentrated, redissolved in hexane/ethyl acetate 1:1 and filtered over a NH$_2$-column (hexane/ethyl acetate 50:50 to 0:100 to pure methanol). The filtrate was concentrated to afford the silylated ethynyl compound, which was then desilylates applying general procedure 8.

General Procedure 7b (GP 7b): Sonogashira Coupling (Conditions B)

The respective iodo-aniline intermediate (1 eq.) was dissolved in THF, together with the respective alkyne (1.5 eq.), followed by dichlorobis(triphenylphosphine)palladium (II) (Pd(PPh$_3$)$_2$Cl$_2$) (0.5 eq.) and a 1M solution of tetra-N-butylammonium fluoride in THF (5 eq.). The mixture was then allowed to react for 40 min at 110° C. in a microwave oven (600 W; max. 6 bar). The crude reaction mixture was directly submitted to preparative HPLC to yield the pure target compound.

General Procedure 8 (GP 8): Desilylation of Trimethylsilyl Alkynes

To a solution of the respective (trimethylsilyl)alkyne in THF (approx. 10 mL per g alkyne) is added a 1M solution of tetra-N-butylammonium fluoride in THF (1 eq.), and the resulting mixture is stirred at room temperature until the reaction is completed (typically after approx. 3 h). The product is isolated by dilution with water, extracted with e.g. ethyl acetate and purified by column chromatography (if required).

Exemplary HPLC Conditions: ("HPLC Conditions A")

Equipment: Analytical Waters HPLC system Acquity with Waters ZQ 2000 single quad MS detector.

Column: Aquity BEH C18 2.1×50 1.7 µm.

Conditions: temperature 60° C.; detection wavelength 214 nm; flow rate 0.8 ml/min; eluents A: 0.1% formic acid in water, B: 0.1% formic acid in ACN; gradient in each case based on B: 1% to 99% (1.6') to 99% (0.4') to 1% (0.1')

LCMS-data given in the subsequent specific experimental conditions refer to HPLC conditions A unless otherwise noted.

Intermediate 1.1

Preparation of [3-(2-Cyano-3,5-difluoro-phenoxy)-phenyl]acetic acid tert-butyl ester

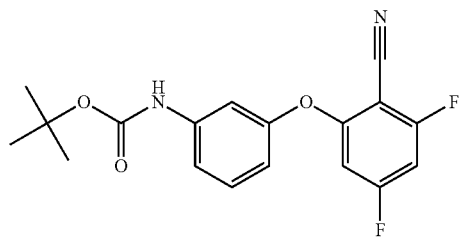 [SMILES: CC(C)(C)OC(=O)Nc1cccc(Oc2cc(F)cc(F)c2C#N)c1]

In analogy to GP 3a, 3.7 g of 2,4,6-trifluorobenzonitrile (23.6 mmol, 1 eq; commercially available) and 5 g of (3-Hydroxy-phenyl)-carbamic acid tert-butyl ester (23.9 mmol, 1.01 eq; commercially available) were dissolved in 63 ml of THF, cooled to 0° C. and treated with 2.08 g sodium hydride (47.56 mmol, 2.02 eq.) and stirred at rt for 17 h. The reaction mixture was poured onto 40 ml of ice water and extracted three times with 100 ml of ethyl acetate each. The organic layer was washed one time with brine, dryed over sodium sulfate, filtered off and concentrated to afford 9.6 g of crude product. The concentrate was purified by flash chromatography (using hexane/ethyl acetate 99/1-50/50) to afford 5.72 g (70% yield, 16.5 mmol) of the desired product.

$^1$H-NMR ($d_6$-DMSO; 300 MHz): 9.57 (s, 1 H); 7.39-7.28 (m, 4 H); 6.80 (ddd, 1 H); 6.62 (ddd, 1 H); 1.43 (s, 9H).

MS (ESI): [M+H]$^+$=347.

Intermediate 1.2

Preparation of {3-[2-Cyano-5-fluoro-3-(2-fluoro-4-iodo-phenylamino)-phenoxy]-phenyl}-carbamic acid tert-butyl ester

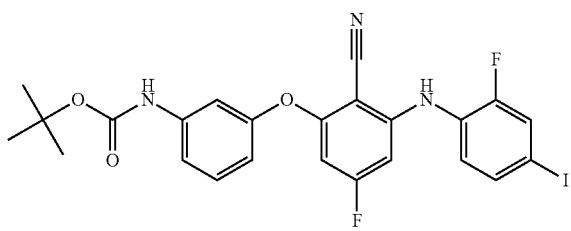 [SMILES: CC(C)(C)OC(=O)Nc1cccc(Oc2cc(F)cc(Nc3ccc(I)cc3F)c2C#N)c1]

In analogy to GP 1, 500 mg of [3-(2-Cyano-3,5-difluorophenoxy)-phenyl]-acetic acid tert-butyl ester (1.44 mmol, 1 eq) and 513 mg of 2-fluoro-4-iodo-benzenamine (2.17 mmol, 1.5 eq; commercially available) were dissolved in 13 ml of THF. Upon cooling to 3° C., 486 mg (4.33 mmol, 3 eq.) of potassium tert-butoxide were added and the mixture stirred for 30 min at this temperature. The mixture was allowed to come to rt slowly and was stirred for another 20 h at rt. After addition of 162 mg (1.44 mmol, 1 eq.) of potassium tert-butoxide the mixture was stirred at rt for another 2 h. The reaction mixture was poured onto 30 ml of ice water and 30 ml ethyl acetate were added. The aqueous phase was extracted three times with 40 ml of ethyl acetate each. The combined organic layers were washed one time with brine, dried over sodium sulfate, filtered off and concentrated to afford 750 mg of crude product. The crude product was purified by flash chromatography (hexane/ethyl acetate 99/1-60/40) to afford 406 g (50% yield, 0.72 mmol) of the desired product.

$^1$H-NMR ($d_6$-DMSO; 300 MHz): 9.54 (s, 1 H); 8.77 (s, 1 H); 7.69 (dd, 1 H); 7.53 (dbr, 1H); 7.34-7.24 (m, 3 H); 7.11 (dd, 1 H); 6.75 (ddd, 1 H); 6.21 (ddd, 1 H); 6.07 (dd, 1 H); 1.43 (s, 9H).

MS (ESI): [M+H]$^+$=564.

Intermediate 1.3

Preparation of {3-[2-Carbamoyl-5-fluoro-3-(2-fluoro-4-iodo-phenylamino)-phenoxy]-phenyl}-carbamic acid tert-butyl ester

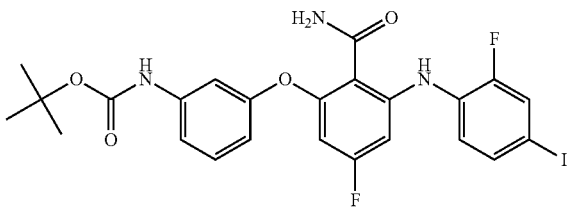 [SMILES: CC(C)(C)OC(=O)Nc1cccc(Oc2cc(F)cc(Nc3ccc(I)cc3F)c2C(N)=O)c1]

In analogy to GP 5, 386 mg of {3-[2-Cyano-5-fluoro-3-(2-fluoro-4-iodo-phenylamino)-phenoxy]-phenyl}-carbamic acid tert-butyl ester (0.69 mmol, 1 eq) were dissolved in 4.8 ml of DMSO and 0.24 ml of 3 M aq. sodium hydroxide solution (0.72 mmol, 10-80 eq) were added. The mixture was heated to 63° C. and 1.85 ml of hydrogen peroxide solution (aq., 30%) were added over the course of 20 min. The mixture was stirred for another 2 h at 65° C. (bath temp.). The reaction mixture was poured onto 175 ml of ice water. 300 ml of ethyl acetate were added and the phases separated. The aqueous phase was extracted one more time with 150 ml of ethyl acetate. The combined organic layers were washed one time with brine, dried over sodium sulfate, filtered off and concentrated. The concentrate was purified (FlashMaster column chromatography, hexane/ethyl acetate 99/1-60/40) to afford 169 mg (42% yield, 0.29 mmol) of the desired product.

$^1$H-NMR ($d_6$-DMSO; 300 MHz): 9.46 (s, 1 H); 9.12 (s, 1 H); 7.83 (sbr, 2 H); 7.66 (dd, 1 H); 7.47 (dbr, 1 H); 7.30-7.17 (m, 4 H); 6.65 (ddd, 1 H); 6.54 (dbr, 1 H); 6.06 (dd, 1 H); 1.42 (s, 9H).

MS (ESI): [M+H]$^+$=582.

Intermediate 1.4

Preparation of 2-(3-Amino-phenoxy)-4-fluoro-6-(2-fluoro-4-iodo-phenylamino)-benzamide

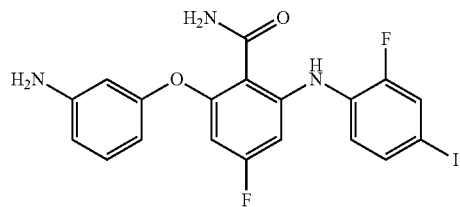 [SMILES: NC(=O)c1c(Nc2ccc(I)cc2F)cc(F)cc1Oc1cccc(N)c1]

In analogy to GP 4, 163 mg of {3-[2-Carbamoyl-5-fluoro-3-(2-fluoro-4-iodo-phenylamino)-phenoxy]-phenyl}-carbamic acid tert-butyl ester (0.28 mmol) were suspended in dichloromethane, 0.29 ml of TFA (3.78 mmol, 13 eq.) were added and the mixture was stirred at rt for 4 h. The reaction mixture was concentrated, redissolved in dichloromethane and sodium hydroxide solution (1M, aq.) was added. After phase separation the organic phase was concentrated to afford 129 mg (96%, 0.27 mmol) of the desired product, which required no further purification.

$^1$H-NMR (d$_6$-DMSO; 300 MHz): 9.23 (s, 1 H); 7.84 (sbr, 1 H); 7.77 (sbr, 1 H); 7.66 (dd, 1 H); 7.47 (dbr, 1 H); 7.21 (dd, 1 H); 7.04 (dd, 1 H); 6.53 (dbr, 1 H); 6.42 (dbr, 1 H); 6.31-6.26 (m, 2 H); 6.07 (dd, 1 H).

MS (ESI): [M+H]$^+$=482.

Transformation of Intermediate 1.4 into example compounds of the present invention was achieved as described below. An alternative synthetic sequence for Intermediate 1.4 is described in the following paragraphs.

Intermediate 2.1

Preparation of 2,4-Difluoro-6-(2-fluoro-4-iodo-phenylamino)-benzonitrile

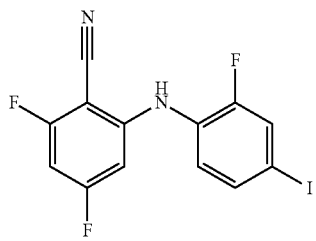 [SMILES: N#Cc1c(F)cc(F)cc1Nc1ccc(I)cc1F]

In analogy to GP 1, 1 g of 2,4,6-trifluoro-benzonitrile (6.37 mmol; 1 eq.; commercially available) and 2.26 g 2-fluoro-4-iodo-benzenamine (9.55 mmol, 1.5 eq; commercially available) were dissolved in 100 ml of THF. The mixture was cooled to −65° C.; 2.14 g of potassium tert-butoxide (19.1 mmol, 3 eq; commercially available) were added. The mixture was stirred for 35 min at this temperature and another 21 h at RT. The mixture was stirred into 120 ml of ice water and extracted three times with ethyl acetate (100 ml each). The combined organic layers were washed with brine, dried over sodium sulfate and concentrated to afford 4.137 g of crude product. Purification was achieved by flash chromatography (hexane/ethyl acetate) to afford 646 mg (27.13% yield; 1.73 mmol) of the target compound.

$^1$H-NMR (d$_6$-DMSO; 300 MHz): 9.02 (s, 1 H); 7.75 (dd, 1 H); 7.58 (dd, 1 H); 7.14 (t, 1 H); 6.95 (td, 1 H); 6.40 (br. d, 1 H).

MS (ESI): [M+H]$^+$=375.

Intermediate 2.2

Preparation of 2-(2-Cyano-3,5-difluoro-phenyl)-(2-fluoro-4-iodo-phenyl)-carbamic acid tert-butyl ester

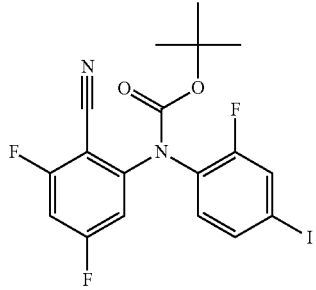 [SMILES: CC(C)(C)OC(=O)N(c1ccc(I)cc1F)c1cc(F)cc(F)c1C#N]

In analogy to GP 9, 205 mg of 2,4-Difluoro-6-(2-fluoro-4-iodo-phenylamino)-benzonitrile (0.55 mmol; 1 eq.) were dissolved in THF under argon and 19 mg DMAP (0.16 mmol; 0.28 eq.) as well as 186 mg of di-tert-butyldicarbonate (0.85 mmol; 1.56 eq.) were added. The mixture was stirred at RT for 20 h. The mixture was concentrated and purified by flash chromatography (5 g Si-column, using hexane/ethyl acetate 100/0-70/30) to afford 253 mg (97% yield, 0.53 mmol) of the desired product.

$^1$H-NMR (d$_6$-DMSO; 300 MHz): 7.77 (br. d, 1 H); 7.56-7.66 (m, 2 H); 7.25 (br. d, 1 H); 7.17 (t, 1 H); 1.36 (s, 9 H).

MS (ESI): [M+H]$^+$=475.

Intermediate 2.3

Preparation of [3-(3-tert-Butoxycarbonylamino-phenoxy)-2-cyano-5-fluoro-phenyl]-(2-fluoro-4-iodo-phenyl)-carbamic acid tert-butyl ester

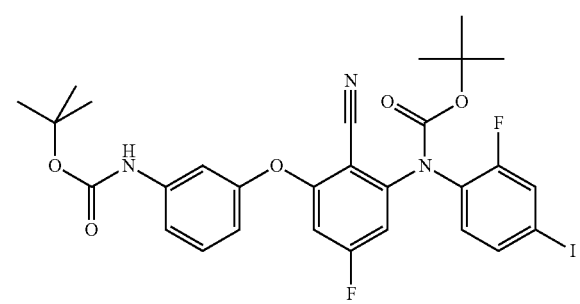 [SMILES: CC(C)(C)OC(=O)Nc1cccc(Oc2cc(F)cc(N(C(=O)OC(C)(C)C)c3ccc(I)cc3F)c2C#N)c1]

500 mg 2(2-Cyano-3,5-difluoro-phenyl)-(2-fluoro-4-iodo-phenyl)-carbamic acid tert-butyl ester (1.05 mmol, 1 eq.) and 412 mg Cs$_2$CO$_3$ (1.27 mmol, 1.2 eq) were dissolved in 5.5 mL DMF and treated with 265 mg (3-hydroxy-phenyl)-carbamic acid tert-butyl ester (1.27 mmol. 1.2 eq.) dissolved in 5.5 mL DMF. The resulting mixture is stirred at 50° C. for 16 h. Extractive workup provided a crude product containing the desired target compound as a mixture of regioisomers along with a smaller fraction of the product of double substitution. This mixture was advanced without further purification.

MS (LC-MS): [M+H]$^+$=664.

Intermediate 2.4 and 2.5 (=being identical to Intermediate 1.4)

Preparation of 2-(3-Amino-phenoxy)-4-fluoro-6-(2-fluoro-4-iodo-phenylamino)-benzonitrile and 2-(3-Amino-phenoxy)-4-fluoro-6-(2-fluoro-4-iodo-phenylamino)-benzamide Intermediate 2.4

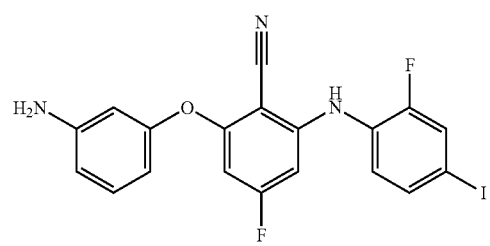

37

Intermediate 2.5

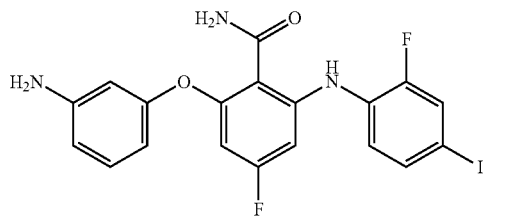 [SMILES: NC(=O)c1c(Nc2ccc(I)cc2F)cc(F)cc1Oc1cncc(N)c1]

200 mg of the crude reaction mixture from the preparation of Intermediate 2.3 were dissolved in 2 mL dioxane and treated with 2.5 mL 4 N HCl (in dioxane). The resulting mixture was stirred at rt overnight. LCMS analysis showed complete removal of both Boc groups as well as partial hydrolysis of the nitrile group to the amide. Extractive work-up, concentration and chromatography of the residue gave rise to Intermediate 2.4 (28% yield) as a mixture of regioisomers and to Intermediate 2.5 (37% yield) as a mixture of regioisomers.

29 mg of the isolated Intermediate 2.4 (0.063 mmol, 1 eq.) were dissolved in 0.75 mL DMSO and treated with 22 μL 3N NaOH solution and 0.52 mL $H_2O_2$ solution and stirred at 65° C. for 2 h. The reaction mixture was diluted with dichloromethane and washed with water. The organic layer was dried and concentrated in vacuo to give 19 mg of Intermediate 2.5 (1.5:1.0 regioisomeric mixture). The regioisomers were either separated on this step by HPLC or after subsequent transformations.

MS (LC-MS) [M+H]$^+$=482.

A further alternative synthetic route for Intermediate 1.3 is described in the subsequent paragraphs:

The following intermediate 3.1 and 3.2 were prepared in analogy to the general procedures described above by using either 5-amino-pyridin-3-ol as nucleophilic starting material.

38

Example Compound 1.1

Preparation of 2-(3-ethanesulfonylamino-phenoxy)-4-fluoro-6-(2-fluoro-4-iodo-phenylamino)-benzamide

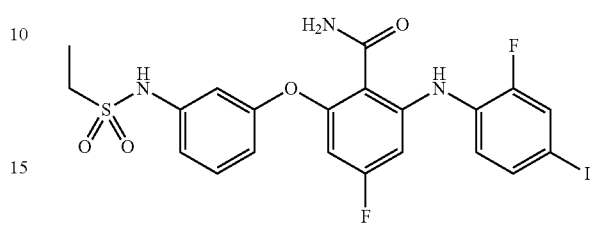

In analogy to GP 6a, 240 mg of 2-(3-amino-phenoxy)-4-fluoro-6-(2-fluoro-4-iodo-phenylamino)-benzamide (Intermediate 1.4; 0.5 mmol, 1 eq.) were dissolved in 8 mL THF and treated with 0.1 mL triethylamine (0.75 mmol, 1.5 eq.) and 71 μL ethylsulfonyl chloride (0.75 mmol, 1.5 eq.). The reaction mixture was stirred at rt overnight, diluted with ethyl acetate, washed with saturated NaHCO$_3$ solution, dried and concentrated in vacuo. HPLC purification of the residue provided 123 mg (0.22 mmol, 48% yield) of the desired compound.

$^1$H-NMR (d$_6$-DMSO; 300 MHz): 9.92 (s, 1 H); 9.03 (s, 1 H); 7.87 (br. s, 1 H); 7.83 (br. s, 1 H); 7.66 (dd, 1 H); 7.47 (br. d, 1 H); 7.31 (t, 1 H); 7.20 (t, 1 H); 6.98 (d, 1 H); 6.94 (t, 1 H); 6.74 (ddd, 1 H); 6.57 (ddd, 1 H); 6.15 (dd, 1 H); 3.10 (q, 2 H); 1.15 (t, 3 H).

MS (LC-MS): [M+H]$^+$=574.

| Intermediate | Structure | Name | Analytical Data |
|---|---|---|---|
| 3.1 | ![structure] | 2-(5-Amino-pyridin-3-yloxy)-4-fluoro-6-(2-fluoro-4-iodo-phenylamino)-benzamide | $^1$H-NMR (d$_6$-DMSO; 300 MHz): 9.03 (s, 1 H); 7.84 (sbr, 2 H); 7.71 (d, 1 H); 7.66 (dd, 1 H); 7.55 (d, 1 H); 7.47 (dbr, 1 H); 7.20 (dd, 1 H); 6.56 (dbr, 1 H); 6.53 (dd, 1 H); 6.19 (dd, 1 H); 5.52 (s, 2 H). MS (LC-MS): [M + H]$^+$ = 483. |
| 3.2 | ![structure] | 2-(3-Amino-benzyloxy)-4-fluoro-6-(2-fluoro-4-iodo-phenylamino)-benzamide | $^1$H-NMR (d$_6$-DMSO; 300 MHz): 9.84 (s, 1 H); 7.73 (sbr, 1 H); 7.72 (sbr, 1 H); 7.64 (dd, 1 H); 7.45 (dbr, 1 H); 7.18 (dd, 1 H); 6.99 (dd, 1 H); 6.61-6.46 (m, 4 H); 6.40 (dbr, 1 H); 5.10 (s, 2 H); 5.01 (s, 2 H). MS (LC-MS): [M + H]$^+$ = 496. |

Example Compound 1.2

Preparation of 4-fluoro-2-(2-fluoro-4-iodo-phenylamino)-6-[3-(propane-2-sulfonylamino)-phenoxy]-benzamide

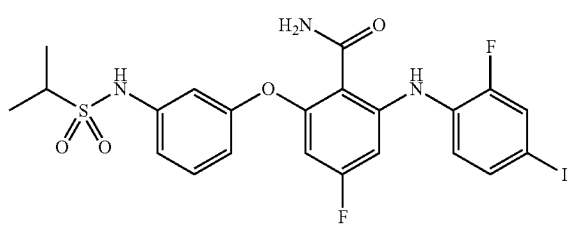 [SMILES: CC(C)S(=O)(=O)Nc1cccc(Oc2cc(F)cc(Nc3ccc(I)cc3F)c2C(N)=O)c1]

In analogy to GP 6b, 144 mg of 2-(3-amino-phenoxy)-4-fluoro-6-(2-fluoro-4-iodo-phenylamino)-benzamide (Intermediate 1.4; 0.3 mmol, 1 eq.) were dissolved in 1.5 mL pyridine and treated with 51 mg iso-propylsulfonyl chloride (0.36 mmol, 1.2 eq., dissolved in 0.5 mL pyridine). The reaction mixture was stirred at rt overnight, treated with another 0.5 eq. sulfonylchloride (in 0.2 mL pyridine) and stirring was continued at rt overnight. After addition of further 0.5 eq. sulfonylchloride (in 0.2 mL pyridine) and further stirring at rt overnight, the resulting mixture diluted with ethyl acetate, washed with water and the organic layers dried. Concentration in vacuo followed by HPLC purification provided 82 mg (46% yield) of the desired compound, which includes substoichiometric amounts of formic acid.

$^1$H-NMR (d$_6$-DMSO; 300 MHz): 9.02 (s, 1 H); 7.88 (br. s, 1 H); 7.84 (br. s, 1 H); 7.65 (dd, 1 H); 7.47 (br. d, 1 H); 7.30 (t, 1 H); 7.21 (t, 1 H); 6.99 (d, 1 H); 6.96 (t, 1 H); 6.73 (ddd, 1 H); 6.57 (ddd, 1 H); 6.13 (dd, 1 H); 3.26 (pent., 1 H); 1.20 (t, 3 H).

MS (LC-MS): [M+H]$^+$=588.

Example Compound 2.1

Preparation of 4-fluoro-2-(2-fluoro-4-iodo-phenylamino)-6-[5-(propane-2-sulfonylamino)-pyridin-3-yloxy]-benzamide

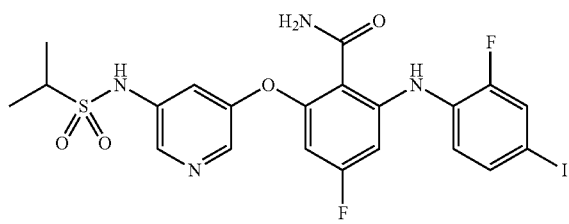 [SMILES: CC(C)S(=O)(=O)Nc1cncc(Oc2cc(F)cc(Nc3ccc(I)cc3F)c2C(N)=O)c1]

In analogy to GP 6b, 100 mg of 2-(5-Amino-pyridin-3-yloxy)-4-fluoro-6-(2-fluoro-4-iodo-phenylamino)-benzamide (Intermediate 3.1; 0.21 mmol, 1 eq.) were dissolved in 1.5 mL pyridine and treated with 37 mg iso-propylsulfonyl chloride (0.26 mmol, 1.25 eq., dissolved in 0.5 mL pyridine). The reaction mixture was stirred at rt overnight, treated with another 1.25 eq. sulfonylchloride (in 0.2 mL pyridine) and stirring was continued at rt overnight. After addition of further 1.25 eq. sulfonylchloride (in 0.2 mL pyridine) and further stirring at rt for 3 days, the resulting mixture diluted with ethyl acetate, washed with water and the organic layers dried. Concentration in vacuo was followed by prepurification by chromatography and subsequent HPLC purification to provide the desired compound.

$^1$H-NMR (d$_6$-DMSO; 300 MHz): 8.87 (s, 1 H); 8.21 (s, 1 H); 8.07 (s, 1 H); 7.96 (s, 1 H); 7.85 (s, 1 H); 7.66 (dd, 1 H); 7.47 (d, 1 H); 7.34 (s, 1 H); 7.20 (t, 1 H); 6.59 (d, 1 H); 6.29 (d, 1 H); 1.21 (d, 6 H) [iso-Propyl CH obscured by solvent signal].

MS (LC-MS): [M+H]$^+$=589.

Example Compound 3.1

Preparation of 2-(3-ethanesulfonylamino-benzyloxy)-4-fluoro-6-(2-fluoro-4-iodo-phenylamino)-benzamide

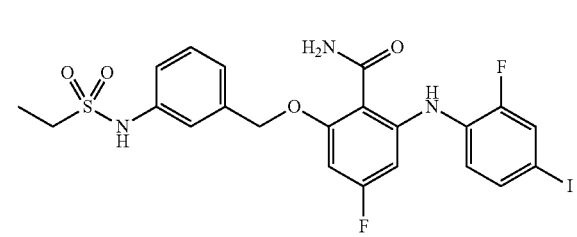 [SMILES: CCS(=O)(=O)Nc1cccc(COc2cc(F)cc(Nc3ccc(I)cc3F)c2C(N)=O)c1]

In analogy to GP 6b, 89 mg of 2-(3-Amino-benzyloxy)-4-fluoro-6-(2-fluoro-4-iodo-phenylamino)-benzamide (Intermediate 3.2; 0.18 mmol, 1 eq.) were dissolved in 0.75 mL pyridine, treated with 34 µL ethylsulfonyl chloride (0.36 mmol, 2 eq.). and stirred at rt for two days. the resulting mixture diluted with ethyl acetate, washed with water and the organic layers dried. Concentration in vacuo was followed by trituration to provide 84 mg of the desired compound (80% yield) with a melting point of 170° C.

$^1$H-NMR (d$_6$-DMSO; 400 MHz): 9.85 (br. s, 1 H); 9.57 (s, 1 H); 7.72 (br. s, 2 H); 7.64 (dd, 1 H); 7.45 (d, 1 H); 7.31 (t, 1 H); 7.26 (s, 1 H); 7.12-7.20 (m, 3 H); 6.56 (dd, 1 H); 6.42 (dd, 1 H); 5.13 (s, 2 H); 3.05 (q, 2 H); 1.14 (t, 3 H).

MS (LC-MS): [M+H]$^+$=588.

Biological Evaluation

The utility of the compounds of the present invention can be illustrated, for example, by their activity in vitro in the in vitro tumor cell proliferation assay described below. The link between activity in tumor cell proliferation assays in vitro and anti-tumor activity in the clinical setting has been very well established in the art. For example, the therapeutic utility of taxol (Silvestrini et al. Stem Cells 1993, 11(6), 528-35), taxotere (Bissery et al. Anti Cancer Drugs 1995, 6(3), 339), and topoisomerase inhibitors (Edelman et al. Cancer Chemother. Pharmacol. 1996, 37(5), 385-93) were demonstrated with the use of in vitro tumor proliferation assays.

Demonstration of the activity of the compounds of the present invention may be accomplished through in vitro, ex vivo, and in vivo assays that are well known in the art. For example, to demonstrate the activity of the compounds of the present invention, the following assays may be used.

Biological Assays

Assay 1

MEK1 Activation Kinase Assay

The kinase Cot1 activates MEK1 by phosphorylating its activation loop. The inhibitory activity of compounds of the present invention on this activation of MEK1 was quantified employing the HTRF assay described in the following paragraphs.

N-terminally His6-tagged recombinant kinase domain of the human Cot1 (amino acids 30-397, purchased from Millipore, cat. no 14-703) expressed in insect cells (SF21) and purified by Ni-NTA affinity chromatography was used as kinase. As substrate for the kinase reaction the unactive C-terminally His6-tagged GST-MEK1 fusion protein (Millipore cat. no 14-420) was used.

For the assay 50 nl of a 100fold concentrated solution of the test compound in DMSO was pipetted into a black low volume 384well microtiter plate (Greiner Bio-One, Frickenhausen, Germany), 3 µl of a solution of 24 nM GST-MEK1 and 166.7 µM adenosine-tri-phosphate (ATP) in assay buffer [50 mM Tris/HCl pH 7.5, 10 mM $MgCl_2$, 2 mM dithiothreitol, 0.01% (v/v) Igepal CA 630 (Sigma), 5 mM β-phospho-glycerol] were added and the mixture was incubated for 10 min at 22° C. to allow pre-binding of the test compounds to the GST-MEK1 before the start of the kinase reaction. Then the kinase reaction was started by the addition of 2 µl of a solution of Cot1 in assay buffer and the resulting mixture was incubated for a reaction time of 20 min at 22° C. The concentration of Cot1 in the assay was adjusted depending of the activity of the enzyme lot and was chosen appropriate to have the assay in the linear range, typical enzyme concentrations were in the range of about 2 ng/µl (final conc. in the 5 µl assay volume). The reaction was stopped by the addition of 5 µl of a solution of HTRF detection reagents (13 nM anti GST-XL665 [# 61GSTXLB, Fa. Cis Biointernational, Marcoule, France], 1 nM Eu-cryptate labelled anti-phospho-MEK 1/2 (Ser217/221) [#61P17KAZ, Fa. Cis Biointernational],) in an aqueous EDTA-solution (100 mM EDTA, 500 mM KF, 0.2% (w/v) bovine serum albumin in 100 mM HEPES/NaOH pH 7.5).

The resulting mixture was incubated 2 h at 22° C. to allow the binding of the phosphorylated GST-MEK1 to the anti-GST-XL665 and the Eu-cryptate labelled anti-phospho-MEK 1/2 antibody. Subsequently the amount of Ser217/Ser221-phosphorylated substrate was evaluated by measurement of the resonance energy transfer from the Eu-Cryptate-labelled anti-phospho-MEK antibody to the anti-GST-XL665. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Normally test compound were tested on the same microtiter plate at 10 different concentrations in the range of 20 µM to 1 nM (20 µM, 6.7 µM, 2.2 µM, 0.74 µM, 0.25 µM, 82 nM, 27 nM, 9.2 nM, 3.1 nM and 1 nM, dilution series prepared before the assay at the level of the 100fold conc. stock solutions by serial 1:3 dilutions) in duplicate values for each concentration and $IC_{50}$ values were calculated by a 4 parameter fit using an inhouse software.

Compound of the present invention were found to be potent MEK inhibitors. The above described example compounds 1.1, 1.2, 2.1 and 3.1 show an IC50 below 300 nM in this assay.

Assay 2
Phospho-ERK Mechanistic Assay

A375 and Colo205 cells were plated in RPMI 1640 growth medium supplemented with 10% FBS at 25,000 cells per well in 96-well tissue culture plates. Cells were incubated overnight in a humidified incubator containing 5% $CO_2$ at 37° C. The following day, to prepare the assay plates, anti-rabbit Meso-Scale Discovery (MSD) plates (cat# L41RA-1, Meso-Scale Discovery, Gaithersburg, Md.) were blocked with 100 µl of 5% MSD blocking buffer for 1 h at room temperature, after which they were washed three times with 200 µl of TBST buffer. The phospho-ERK rabbit polyclonal antibody (cat# 9101, Cell Signaling Technologies, Danvers, Mass.) diluted at 1:200 into 2.5% of MSD Blocker A-TBST was added (25 µl) to each well and the plate was then incubated 1 h at room temperature with shaking. The plates were then washed once with phosphate buffered saline (PBS) and ready to receive the cell lysates. While the preparation of the assay plates was ongoing, test compounds were added to the wells of cell-containing plates from the previous day, serially diluted in RPMI 1640 medium containing 10% FBS, 0.1% bovine serum albumin (BSA) and 0.03% DMSO and the plates were incubated for 1.5 h at 37° C. After this incubation, the compound-treated plates were washed three times with PBS, lysed in 30 µl of Bio-Rad lysis buffer (cat #98601, Bio-Rad Laboratories, Hercules, Calif.) and then left shaking on ice for 30 min. The lysates were then loaded on the phospho-ERK coated MSD plates and the plates Incubated overnight at 4° C. The following day, the plates were washed three times with TBST and 25 µl of 1:3000 diluted total ERK monoclonal antibody (Cat# 610123, BD Biosciences, San Diego, Calif.) was added to the plates that were then incubated 1 h at room temperature with shaking. After the incubation the plates were washed three times with TBST as described earlier and 25 µl of MSD sulfo-tag anti-mouse antibody (cat #R32AC-5) diluted 1:1000 were added into each well. The plates were Incubated 1 h at room temperature with shaking, then washed four times with TBST. Just prior to reading the plates, 150 µl of MSD Read buffer T was added and the plates were read immediately on the MSD instrument. Data analysis was performed using Analyze5 software for $IC_{50}$ analysis.

Assay 3
Alternative Conditions for Mechanistic Perk Assay

For the measurement of ERK1/2 phosphorylation in tumor cell lines a singleplex Mesoscale Discovery (MSD) assay is used. This assay is built up like a sandwich immunoassay. Cell lysates generated from different tumor cell lines treated with serially diluted MEK inhibitor compounds were loaded on the MSD plates. Phosphorylated ERK1/2 present in the samples binds to the capture antibody immobilized on the working electrode surface. The sandwich is completed by binding of a detection antibody to the immobilized phospho-ERK1/2. This detection antibody is labeled with an electrochemiluminescent compound. Applying voltage to the plate electrodes causes the labels, bound to the electrode surface via the antibody-phospho ERK1/2 sandwich complex, to emit light. The measurement of the emitted light allows a quantitative determination of the amount of phosphorylated ERK1/2 present in the sample. In detail, a linear range for the measurement of phosphoERK signals must be determined for every cell line used in the assay by titrating different cell numbers. For the final assay, the previously determined cell number is seeded in 96 well plates. 24 h after seeding, cells were treated for 1.5 h with serially diluted allosteric MEK inhibitor compounds before the cells were lysed and lysates were transferred in the MSD assay plate. The manufacturer's protocol was changed in that the binding step of the phosphorylated ERK to the capture antibody was performed over night at 4° C. instead of 3 h at room temperature, leading to a better signal strength.

A375 or Colo205 cells were plated in 50 µL DMEM growth medium (Biochrom FG 0435) supplemented with 10% FBS (Biochrom #S0410) (A375), respectively in RPMI growth medium (Biochrom FG1215) supplemented with 10% FBS (Biochrom #S0410), 10 mM HEPES (Biochrom L1613), 4.5 g/L Glucose and 1 mM sodiumpyruvat (Biochrom L0473) (Colo-205) at 45000 cells per well in 96-well tissue culture plates. Cells were incubated overnight in a humidified incubator containing 5% $CO_2$ at 37° C.

The Phospho-ERK by Mesoscale Discovery (MSD) (# K111DWD) assay was performed according to the manufacturer's recommendations. In brief the protocol was:

The day after cell seeding, to prepare the assay plates, MSD were blocked with 150 µl of MSD blocking buffer for 1 h at room temperature, after which they were washed four times with 150 µl of Tris Wash buffer. While the preparation of the assay plates was ongoing, test compounds were added to the wells of cell-containing plates from the previous day, serially diluted in respective growth medium containing 10% FBS and 0.1% DMSO and the plates were incubated for 1.5-2 h at 37° C. After this incubation the medium was aspirated, cells were lysed in 50 µl lysis buffer and then left shaking for 30 min at 4° C. 25 µL of the lysates were then loaded on the blocked MSD plates and the plates Incubated overnight at 4° C. The following day, the plates were washed four times with Tris wash buffer and 25 µl detection antibody solution was added to the plates that were then incubated 1 h at room temperature with shaking. After the incubation the plates were washed four times with Tris wash buffer 150 µl of MSD Read buffer T was added and the plates were read immediately on the MSD instrument. Data analysis was performed using an in-house software for IC50 analysis.

Assay 4

In vitro Tumor Cell Proliferation Assay:

The adherent tumor cell proliferation assay used to test the compounds of the present invention involves a readout called Cell Titre-Glo developed by Promega (Cunningham, B A "A Growing Issue: Cell Proliferation Assays. Modern kits ease quantification of cell growth" *The Scientist* 2001, 15(13), 26, and Crouch, S P et al., "The use of ATP bioluminescence as a measure of cell proliferation and cytotoxicity" *Journal of Immunological Methods* 1993, 160, 81-88).

A375 and Colo205 cells were plated in RPMI 1640 growth medium supplemented with 10% FBS at 3,000 cells per well in 96-well tissue culture plates. Cells were incubated overnight in a humidified incubator containing 5% $CO_2$ at 37° C. The following day, test compounds were added to wells, serially diluted in RPMI 1640 medium containing 10% FBS and 0.03% DMSO and the plates were incubated for 72 h at 37° C. Evaluation of cell density was made at different time points (0 and 72 h post-dosing) by adding to each well 150 µl of Cell Titer Glo reagent (cat# G7572, Promega, Madison Wis.) followed by incubation of the plates on a rotator for 10 min at room temperature and then reading of the luminescence on a Victor3 instrument. Data analysis was performed using Analyze5 software for $IC_{50}$ analysis.

Assay 5

In vitro Tumor Cell Proliferation Assay in A375 Cells (Cell Titer Glow [CTG] Assay)

A375 cells [human malignant melanoma cells, ATCC # CRL-1619, expressing mutant BRAF V600E] were plated at a density of 3000 cells/well in 96 well black-clear bottom tissue culture plates (Costar 3603 black/clear bottom) in 100 µL/well DMEM medium (Biochrom; FG0435; +3.7 g/L odium bicarbonate; +4.5 g/L D-Glucose) with 10% Fetal Bovine Serum (FBS) and stable Glutaminincubated at 37° C. Plate sister wells in separate plate for time zero determination. Incubate all plates overnight 37° C. Take down time zero plate: add 67 µL/well CTG solution (Promega Cell Titer Glo solution) to time zero wells in sister plate; the plates were mixed for 2 min on orbital shaker to ensure cell lysis, incubate 10 minutes, read luminescence on VICTOR 3 (Perkin Elmer). Twenty-four hours after cell seeding, test compounds diluted in 50 µL medium are added at a final concentration range from as high 10 µM to as low 300 µM depending on the activities of the tested compounds in serial dilutions at a final DMSO concentration of 0.4%. Cells were incubated for 72 hours at 37° C. after addition of the test compound. Then, using a Promega Cell Titer Glo Luminescent® assay kit, 100 microliters lysis buffer containing of the enzyme luciferase and its substrate, luciferin mixture, were added to each well and incubated for 10 min at room temperature in the dark to stabilize luminescence signal. The samples were read on VICTOR 3 (Perkin Elmer) using Luminescence protocol. The percentage change in cell growth was calculated by normalizing the measurements to the extinctions of the zero point plate (=0%) and the extinction of the untreated (0 µM) cells (=100%). The IC50 values were determined by means of a 4-parameter fit using the company's own software.

Alternatively, the Cell Proliferation was Measured by Crystal Violet (CV) Staining: Assay 6

Cultivated human A375 cells were plated out in a density of 1500 cells/measurement point in 200 µl of growth medium (DMEM/HAMS F12 (Biochrom; FG4815) with 10% FBS and 2 mM Glutamine) in a 96-well multititer plate. After 24 hours, the cells from a plate (zero plate) were stained with crystal violet (see below), while the medium in the other plates was replaced by fresh culture medium (200 µl) to which the test substances had been added in various concentrations (0 µM, and in the range 0.3 nM -30 µM; the final concentration of the solvent dimethyl sulphoxide was 0.5%). The cells were incubated in the presence of the test substances for 4 days. The cell proliferation was determined by staining the cells with crystal violet: the cells were fixed by adding 20 µl/measurement point of an 11% glutaraldehyde solution at room temperature for 15 min. After the fixed cells had been washed three times with water, the plates were dried at room temperature. The cells were stained by adding 100 µl/measurement point of a 0.1% crystal violet solution (pH adjusted to pH 3 by adding acetic acid). After the stained cells had been washed three times with water, the plates were dried at room temperature. The dye was dissolved by adding 100 µl/measurement point of a 10% acetic acid solution, and the extinction was determined by photometry at a wavelength of 595 nm. The percentage change in cell growth was calculated by normalizing the measurements to the extinctions of the zero point plate (=0%) and the extinction of the untreated (0 µM) cells (=100%). The IC50 values were determined by means of a 4-parameter fit using the company's own software.

Compounds of the present invention were found to be potent inhibitors of cell proliferation. The following representative example compounds show an IC50 below 100 nM in the A375 proliferation CV assay: Examples 1.1 and 1.2.

In vitro inhibition of proliferation of further cancer cell lines can be measured in analogy to the afore-described procedures. Details for exemplary further tumor cells lines are given below:

| Cells | Indication (all human) | Ras or Raf Mutation | Method | cell number per well | medium |
|---|---|---|---|---|---|
| A-431 | epidermoid cancer | | CTG | 3000 | DMEM/HAMS F12 (Biochrom; FG4815) + 10% FBS and stable Glutamin |
| A-431 non-adherent | epidermoid cancer | | CTG | 3000 | DMEM/HAMS F12 (Biochrom; FG4815) + 10% FBS and stable Glutamin (Plates were coated with poly-2-hydroxy-ethylmethacrylate before cell seeding) |
| A549 | lung carcinoma | KRAS G12S | CTG | 2000 | DMEM/HAMS F12 (Biochrom; FG4815) + 10% FBS and stable Glutamin |
| Colo-205 | colon carcinoma | BRAF V600E | CTG | 3000 | RPMI1640 (Biochrom; FG1215) + 10% heat inactivated FBS and stable glutamin + 1x non-essentiell amino acid + 1 mM Sodiumpyruvat + 10 mM Hepes |
| HCT-116 | colon cancer, | KRAS G13D | CTG | 3000 | DMEM/HAMS F12 (Biochrom; FG4815) + 10% FBS and stable Glutamin |
| HT-29 | colon cancer | BRAF V600E | CTG | 2000 | DMEM/HAMS F12 (Biochrom; FG4815) + 10% FBS and stable Glutamin |
| Lox | Melanoma | BRAF V600E | CTG | 2000 | RPMI1640 (Biochrom; FG1215) + 10% heat inactivated FBS and stable glutamin + 1x non-essentiell amino acid + 1 mM Sodiumpyruvat |
| MCF-7 | breast cancer | | CTG | 5000 | RPMI1640 (F1275; w/o phenol red) + 10% FBS + 2 mM Glutamin + 2 mU/mL Insulin + 1E−10M estradiol |

Assay 7
In vivo Efficacy Studies: Staged Human Xenograft Models

The in vivo anti-tumor activity of lead compounds was assessed in mice using xenograft models of human BRAF mutant melanoma and colon carcinomas. The Female athymic NCR nude mice were implanted subcutaneously with either a human melanoma (LOX), or a human colon (Colo205) carcinoma lines acquired from American Type Culture Collection (ATCC, Maryland). Treatment was initiated when tumors reached approximately 100 mg in size. Compounds were administered orally and freshly prepared in PEG/water (80%/20% respectively). The general health of mice was monitored and mortality was recorded daily. Tumor dimensions and body weights were recorded twice a week starting with the first day of treatment. Animals were euthanized according to Bayer IACUC guidelines. Treatments producing greater than 20% lethality and/or 20% net body weight loss were considered 'toxic'.

Tumor growth was measured with electronic calipers three times a week and tumor weight (mg) calculated according to the following formula: [length (mm)×width (mm)$^2$]/2. Anti-tumor efficacy was determined as a function of tumor growth inhibition (% TGI). TGI is calculated on days of measurement using the following formula: (100−mean tumor value of treated (T)/mean tumor of control value (C)×100)=% T/C. The control used in the calculations is either the "untreated control" or "vehicle", whichever provides the most conservative representation of the data. A compound demonstrating a TGI of greater than or equal to 50% is considered active. Statistical significance is determined using either a one-tailed or two-tailed Student's T-Test. The compounds that were tested showed significant dose-dependent tumor growth inhibition in both LOX and Colo205 models.

Compounds of the invention were tested for activity using one or more of the assay procedures presented above.

It is believed that one skilled in the art, using the preceding information and information available in the art, can utilize the present invention to its fullest extent. Those skilled in the art will recognize that the invention may be practiced with variations on the disclosed structures, materials, compositions and methods without departing from the spirit or scope of the invention as it is set forth herein and such variations are regarded as within the ambit of the invention. The compounds described in the examples are intended to be representative of the invention, and it will be understood that the scope of the invention is not limited by the scope of the examples. The topic headings set forth above are meant as guidance where certain information can be found in the application, but are not intended to be the only source in the application where information on such topics can be found. All publications and patents cited above are incorporated herein by reference.

REFERENCES

[1] American Cancer Society, Cancer Facts and Figures 2005.
[2] Sausville E A, El Sayed Y, Monga M, Kim G. Signal Transduction Directed Cancer Treatments. Annu Rev Pharmacol Toxicol 2002 ; 43: 199-231.
[3] O'Dwyer M E, Mauro M J, Druker B J. STI571 as a targeted therapy for CML. Cancer Invest 2003; 21: 429-438.

[4] de Jong F A, Verweij J. Role of imatinib mesylate (Gleevec/Glivec) in gastrointestinal stromal tumors. Expert Rev Anticancer Ther 2003; 3: 757-766.

[4] Becker J. Signal transduction inhibitors—a work in progress. Nature Biotech 2004; 22: 15-18.

[5] Cobb M H. MAP kinase pathways. Prog Biophys Mol Biol 1999; 71: 479-500.

[6] Lewis T S, Shapiro P S, Ahn N G. Signal transduction through MAP kinase cascades. Adv Cancer Res 1998; 74: 49-139.

[7] English J M, Cobb M H. Pharmacological inhibitors of MAPK pathways. Trends Pharmacol Sci 2002 ; 23: 40-45.

[8] Duesbery N S, Webb C P, Vande Woude G F. MEK wars, a new front in the battle against cancer. Nat Med 1999 ; 5: 736-737.

[9] Sebolt-Leopold J S. Development of anticancer drugs targeting the MAP kinase pathway. Oncogene 2000; 19: 6594-6599.

[10] Milella M, Precupanu C M, Gregorj C, Ricciardi M R, Petrucci M T, Kornblau S M, Tafuri A, Andreeff M. Beyond single pathway inhibition: MEK inhibitors as a platform for the development of pharmacological combinations with synergistic anti-leukemic effects. Curr Pharm Des. 2005; 11(21):2779-95.

[11] Hancock C N, Macias A T, Mackerell A D Jr, Shapiro P. Mitogen activated protein (MAP) kinases: development of ATP and non-ATP dependent inhibitors. Med. Chem. 2006 March; 2(2):213-22.

[12] Deramaudt T, Rustgi A K. Mutant KRAS in the initiation of pancreatic cancer. Biochim Biophys Acta. 2005; 1756 (2):97-101.

[13] Libra M, Malaponte G, Navolanic P M, Gangemi P, Bevelacqua V, Proietti L, Bruni B, Stivala F, Mazzarino M C, Travali S, McCubrey J A. Analysis of BRAF mutation in primary and metastatic melanoma. Cell Cycle. 2005 October ;4(10):1382-4.

[14] Herrera R, Sebolt-Leopold J S. Unraveling the complexities of the Raf/MAP kinase pathway for pharmacological intervention. Trends Mol Med 2002 ; 8: S27-S31.

[15] Alessi D R, Cuenda A, Cohen P, Dudley D T, Saltiel A R. PD 098059 is a specific inhibitor of the activation of mitogenactivated protein kinase kinase in vitro and in vivo. J Biol Chem 1995; 270: 27489-27494.

[16] Favata M F, Horiuchi K Y, Manos E J, Daulerio A J, Stradley D A, Feeser W S, et al. Identification of a novel inhibitor of mitogenactivated protein kinase kinase. J Biol Chem 1998; 273: 18623-18632.

[17] Allen L F, Sebolt-Leopold J, Meyer M B. CI-1040 (PD184352), a targeted signal transduction inhibitor of MEK (MAPKK). Semin Oncol 2003; 30: 105-116.

[18] Sebolt-Leopold J S, Dudley D T, Herrera R, Van Becelaere K, Wiland A, Gowan R C, et al. Blockade of the MAP kinase pathway suppresses growth of colon tumors in vivo. Nat Med 1999; 5: 810-816

[19] Waterhouse D, Rinehart J, Adjei A, Hecht J, Natale R, LoRusso P, et al. A phase 2 study of an oral MEK inhibitor, CI-1040, in patients with advanced non small-cell lung, breast, colon, or pancreatic cancer. Proc Am Soc Clin Oncol 2003; 22: 204a (abstr).

The invention claimed is:
1. A compound of general formula (I) :

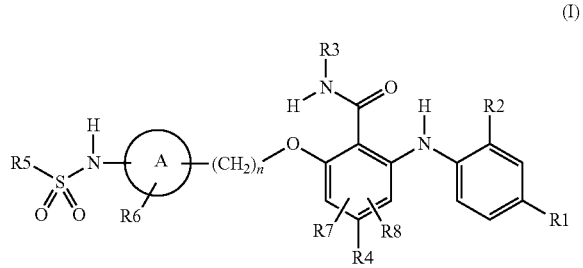

in which:
R1 is selected from the group consisting of halogen or —C≡C—H;
R2 is hydrogen, halogen or alkyl;
wherein at least one of R1 and R2 is halogen;
R3 is hydrogen or alkyl;
R4 is selected from the group consisting of halogen and cyano;
R5 is C2-C6 alkyl;
R6 is selected from the group consisting of hydrogen, halogen, cyano, alkoxy, amino, alkylamino, dialkylamirio;
R7 and R8 independently from each other are hydrogen, halogen or alkyl;
A is selected from the group consisting of aryl and heteroaryl;
n is an integer from 0 to 2.

2. The compound according to claim 1, wherein:
R1 is halogen;
R2 is halogen;
R3 is hydrogen;
R4 is selected from the group consisting of halogen and cyano;
R5 is C2-C6 alkyl;
R6 is selected from the group consisting of hydrogen, halogen, cyano, alkoxy, amino, alkylamino, dialkylamino;
R7 and R8 independently from each other are hydrogen or halogen;
A is selected from the group consisting of aryl and heteroaryl;
n is an integer from 0 to 1.

3. The compound according to claims 1, wherein:
R1 is halogen;
R2 is halogen;
R3 is hydrogen;
R4 is halogen;
R5 is C2-C6 alkyl;
R6 is hydrogen;
R7 and R8 are hydrogen;
A is phenyl or pyridyl;
n is an integer from 0 to 1.

4. The compound according to claims 1, which is selected from the group consisting of:
2-(3-ethanesulfonylamino-phenoxy)-4-fluoro-6-(2-fluoro-4-iodo-phenylamino)-benzamide;
4-fluoro-2-(2-fluoro-4-iodo-phenylamino)-6-[3-(propane-2-sulfonylamino)-phenoxy]-benzamide;
4-fluoro-2-(2-fluoro-4-iodo-phenylamino)-6-[5-(propane-2-sulfonylamino)-pyridin-3-yloxy]-benzamide; and
2-(3-ethanesulfonylamino-benzyloxy)-4-fluoro-6-(2-fluoro-4-iodo-phenylamino)-benzamide.

5. A method of preparing a compound of general formula (I) according to claim 1, said method comprising the step of allowing an intermediate compound of general formula 8:

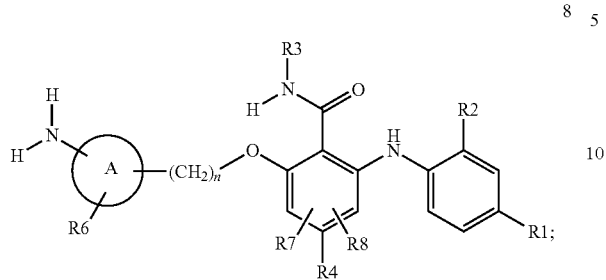

in which R1, R2, R3, R4, R5, R7, R8, A and n are as defined in claim 1, to react in the presence of a base with an sulfonyl chloride of formula 9:

in which R5 is as defined claim 1;
to yield a compound of general formula (I):

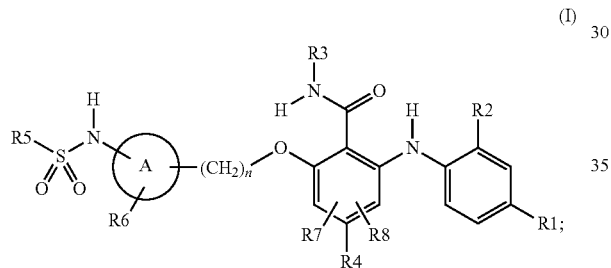

in which R1, R2, R3, R4, R5, R6, R7, R8, A and n are as defined in claim 1.

6. A method of preparing a compound of general formula (Ib), said method comprising the step of allowing an intermediate compound of general formula (Ia):

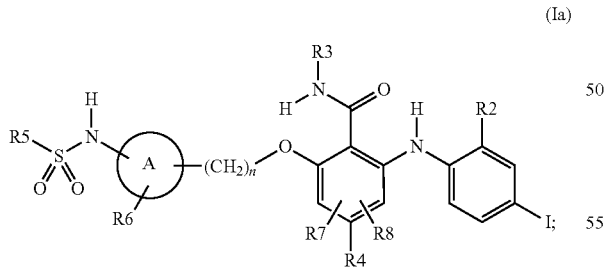

in which R2, R3, R4, R5, R7, R8, A and n are as defined in claim 1, to react with an alkyne of formula 17:

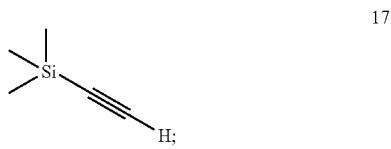

in the presence of a Pd catalyst, copper iodide and a base optionally followed by desilylation to yield a compound of general formula (Ib):

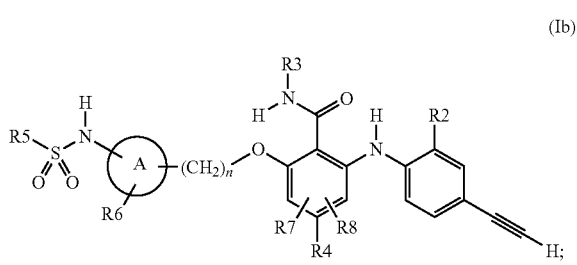

in which R2, R3, R4, R5, R6, R7, R8, A and n are as defined in claim 1.

7. A pharmaceutical composition comprising a compound according to claim 1, or a tautomer, stereoisomer, physiologically acceptable salt, hydrate, solvate, or prodrug thereof, and a pharmaceutically acceptable diluent or carrier.

8. The pharmaceutical composition according to claim 7 wherein said compound is present in a therapeutically effective amount.

9. The pharmaceutical composition according to claim 8 which further comprises at least one further active compound.

10. The pharmaceutical composition according to claim 9, in which said further active compound is an anti-hyperproliferative agent, an anti-angiogenic agent, a mitotic inhibitor, an alkylating agent, an anti-metabolite, a DNA-intercalating antibiotic, a growth factor inhibitor, a cell cycle inhibitor, an enzyme inhibitor, a toposisomerase inhibitor, a biological response modifier, or an anti-hormone.

11. A packaged pharmaceutical composition comprising a container, the pharmaceutical composition of claim 7, and instructions for using the pharmaceutical composition to treat a disease or condition in a mammal.

* * * * *